(12) United States Patent
Actis et al.

(10) Patent No.: US 10,696,962 B2
(45) Date of Patent: Jun. 30, 2020

(54) NANOPIPETTE DEVICE AND METHOD FOR SUBCELLULAR ANALYSIS

(71) Applicant: THE REGENTS OF THE UNIVERSITY OF CALIFORNIA, Oakland, CA (US)

(72) Inventors: Paolo Actis, London (GB); Michelle M. Maalouf, Concord, CA (US); Nader Pourmand, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 882 days.

(21) Appl. No.: 14/775,168

(22) PCT Filed: Mar. 13, 2014

(86) PCT No.: PCT/US2014/025682
§ 371 (c)(1),
(2) Date: Sep. 11, 2015

(87) PCT Pub. No.: WO2014/160036
PCT Pub. Date: Oct. 2, 2014

(65) Prior Publication Data
US 2016/0032275 A1    Feb. 4, 2016

Related U.S. Application Data

(60) Provisional application No. 61/781,841, filed on Mar. 14, 2013.

(51) Int. Cl.
*C12N 15/10* (2006.01)
*C12M 1/00* (2006.01)
(Continued)

(52) U.S. Cl.
CPC ......... *C12N 15/1003* (2013.01); *C12M 47/06* (2013.01); *C12Q 1/686* (2013.01);
(Continued)

(58) Field of Classification Search
USPC .............. 73/863.32, 864.11, 864.24, 864.25; 422/501
See application file for complete search history.

(56) References Cited

U.S. PATENT DOCUMENTS 7,276,206 B2   10/2007   Augustine et al.
7,655,791 B2    2/2010   Makarov et al.
(Continued)

FOREIGN PATENT DOCUMENTS

| JP | 2008271804 A | * 11/2008 | ............ C12M 35/00 |
| WO | 2008054488 A2 | 5/2008 | |
| WO | 2013184065 A1 | 12/2013 | |

OTHER PUBLICATIONS

Actis, P., et al., "Compartmental Genomics in Living Cells Revealed by Single-Cell Nanobiopsy," ACS Nano (Jan. 28, 2014), 8(1):546-553.

(Continued)

*Primary Examiner* — Rebecca L Martinez
(74) *Attorney, Agent, or Firm* — Brian E. Davy; Bozicevic, Field & Francis LLP

(57) ABSTRACT

Described herein are devices and methods for extracting cellular material from living cells and then depositing them into to a receptacle in a nanoliter scale. Using a nanopipette integrated into a scanning ion conductance microscope (SICM), extraction of mitochondrial DNA from human BJ fibroblasts and Green Fluorescent Protein (GFP) transcripts from HeLa/GFP cells was achieved with minimal disruption to the cellular milieu and without chemical treatment prior to obtaining the isolated sample. Success of the extraction was confirmed by fluorescence microscopy and PCR analysis of the extracted material. The method and apparatus may be applied to many different cell types and intracellular targets, allowing not only single cell analysis, but single (Continued)

subcellular compartment analysis of materials extracted in their native state.

45 Claims, 13 Drawing Sheets

Specification includes a Sequence Listing.

(51) Int. Cl.
| | |
|---|---|
| *G01Q 60/44* | (2010.01) |
| *C12Q 1/6806* | (2018.01) |
| *C12Q 1/686* | (2018.01) |
| *C12Q 1/6874* | (2018.01) |
| *C12Q 1/6876* | (2018.01) |
| *G01N 33/573* | (2006.01) |
| *G01N 35/10* | (2006.01) |

(52) U.S. Cl.
CPC ......... *C12Q 1/6806* (2013.01); *C12Q 1/6874* (2013.01); *C12Q 1/6876* (2013.01); *G01N 33/573* (2013.01); *G01Q 60/44* (2013.01); *C12Q 2600/158* (2013.01); *G01N 2035/1034* (2013.01); *G01N 2333/91* (2013.01); *G01N 2440/14* (2013.01)

(56) References Cited

U.S. PATENT DOCUMENTS

| | | | |
|---|---|---|---|
| 8,940,142 B2 | 1/2015 | Karhanek et al. | |
| 8,980,073 B2 | 3/2015 | Pourmand et al. | |
| 2002/0106715 A1* | 8/2002 | Huberman | G01N 15/1468 435/33 |
| 2004/0063100 A1 | 4/2004 | Wang | |
| 2008/0161200 A1 | 7/2008 | Yu et al. | |
| 2010/0072080 A1 | 3/2010 | Karhanek et al. | |
| 2010/0285210 A1 | 11/2010 | Choi | |
| 2010/0331200 A1 | 12/2010 | Gordon et al. | |
| 2012/0010091 A1 | 1/2012 | Linnarson | |
| 2012/0222958 A1 | 9/2012 | Pourmand et al. | |
| 2012/0225435 A1 | 9/2012 | Seger et al. | |
| 2012/0264108 A1 | 10/2012 | Chen et al. | |
| 2015/0177189 A1 | 6/2015 | Pourmand et al. | |

OTHER PUBLICATIONS

Bruckbauer, A., et al., "Multicomponent Submicron Features of Biomolecules Created by Voltage Controlled Deposition from a Nanopipet," J. Am. Chem. Soc. (2003), 125:9834-9839.

Choi, Y., et al., "Biosensing with conically shaped nanopores and nanotubes," Phys. Chem. Chem. Phys. (2006), 8:4976-4988.

Laforge, F., et al., "Electrochemical attosyringe," PNAS (Jul. 17, 2007), 104(29):11895-11900.

Li, S., et al., "Development of boronic acid grafted random copolymer sensing fluid for continuous glucose monitoring," Biomacromolecules (Jan. 2009), 10(1):113-118.

Maillard, M., et al., "Two Liquids Wetting and Low Hysteresis Electrowetting on Dielectric Applications," Langmuir (2009), 25(11):6162-6167.

Matsuoka, H., et al., "Automatic Stop of a Microinjector Distinctively in the Cytosol or the Vacuole of Plant Single-cells," Electrochemistry (2007), 75(7):515-517.

Mulla, H., et al., "3-Methoxycarbonyl-5-nitrophenyl boronic acid: high affinity diol recognition at neutral pH," Bioorganic & Medicinal Chemistry Letters (2004), 14:25-27.

Rodolfa, K., et al., "Two-Component Graded Deposition of Biomolecules with a Double-Barreled Nanopipette," Agnew. Chem. Int. Ed. (2005), 44:6854-6859.

Rodolfa, K., et al., "Nanoscale Pipetting for Controlled Chemistry in Small Arrayed Water Droplets Using a Double-Barrel Pipet," Nano Letters (2006), 6(2):252-257.

Tariq, M., et al., "Whole-transcriptome RNAseq analysis from minute amount of total RNA," Nucleic Acids Research (2011), 1-10.

Umehara, S., et al., "Label-free biosensing with functionalized nanopipette probes," PNAS (Mar. 24, 2009), 106(12):4611-4616.

Ying, L., et al., "The scanned nanopipette: a new tool for high resolution bioimaging and controlled deposition of biomolecules," Phys. Chem. Chem. Phys. (2005), 7:2859-2866.

Ying, L., "Applications of nanopipettes in bionanotechnology," Biochem. Soc. Trans. (2009) 37:702-706.

International Search Report and Written Opinion, International Application No. PCT/US14/25682, dated Jul. 18, 2014.

Francois et al. (2007) "Electrochemical attosyringe" PNAS; 104(29):11895-11900.

Actis, P., et al., "Single-Cell Biopsy using Nanopipettes," Biophysical Journal (2012) 102(3):Abstract.

Chen, C-C., et al., "Scanning Ion Conductance Microscopy," Annual Review of Analytical Chemistry (2012) 5(1):207-228.

Maalouf, M., et al., "Single-cell Manipulation using Nanopipettes," 13th Annual UC Systemwide Bioengineering Symposium (2012) 384-387.

Seger, R.A., et al., "Voltage controlled nano-injection system for single-cell surgery," Nanoscale (2012) 4(19):5843-5846.

* cited by examiner

NANOPIPETTE DEVICE AND METHOD FOR SUBCELLULAR ANALYSIS

CROSS-REFERENCE TO RELATED APPLICATIONS

This application claims priority from U.S. Provisional Patent Application No. 61/781,841 filed on Mar. 14, 2013, which is hereby incorporated by reference in its entirety, and is a U.S. national stage application of PCT/US2014/025682, having an international filing date of Mar. 13, 2014, the disclosure of which is incorporated herein by reference in its entirety.

STATEMENT OF GOVERNMENTAL SUPPORT

This invention was made with Government support under contract HG000205 awarded by the National Institutes of Health, and contract U54CA143803 awarded by the National Cancer Institute. The Government has certain rights in this invention.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Sep. 3, 2015, is named "482_35_1US_Seq_List-.txt" and is 2,184 bytes in size.

BACKGROUND OF THE INVENTION

Field of the Invention

The present invention relates to the field of nanodevices for single cell extraction of intracellular contents, specifically, mitochondrial DNA.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Physiological and pathological processes within the human body are controlled by complex cell-cell interactions within the context of a dynamic microenvironment. Biomolecular analysis of cells has been traditionally conducted under the assumption that cells of a clonal population behave identically. This assumption arose not from experimental evidence but from the lack of tools capable of analyzing individual cells. Furthermore, the ability to dynamically measure phenotypes (i.e. gene expression, protein activities, ion fluctuations, signaling) at the single cell level is key to understanding cellular behavior in a complex environment (1-4).

In 1990, James Eberwine's group isolated a single-cell in culture using a glass micropipette and demonstrated that RNA extracted from that cell could be amplified and analyzed (5). This experiment pioneered the field of single-cell biology and Eberwine's group successfully applied this technology towards understanding the molecular basis of neuronal functioning (6). In the last 20 years, biomolecular analysis leaped forward with the development of high-throughput sequencing which now allows researchers to obtain the collection of active genes in a cell in a single readout (7). The initial capture of the single cell, however, remains a major technical issue (1). Since Eberwine's success using a glass micropipette, scientists have used a variety of techniques to isolate single cells, from enzymatic digestion (which releases cells from tissues) to laser microdissection (which cuts out a homogeneous population of intact cells from tissue sections). However, these methods either cannot examine cells in their native environment, or as with the original micropipette, they are limited to probing isolated cells (8).

Nanodevices as Surgical Tools

Nanoscale devices are ideal single-cell surgical tools because of their potential for high spatial and temporal resolution studies (9-10). Recently two groups independently developed cellular nanoendoscopes for single cell analysis. Singhal et al. (11) attached a carbon nanotube at the very tip of a glass micropipette and showed its potential for interrogating cells, transporting fluids and performing optical and electrochemical diagnostics down to the single organelle level. Similarly Yan et al. (12) developed a nanowire waveguide attached to the tip of an optical fiber which can both guide visible light into intracellular compartments of a living mammalian cell and detect optical signals from sub-cellular regions. The cylindrical shape of these nanoendoscopes allows the probing of organelles deep inside the cell but these technologies lack any automation capability; these endoscopes are manually positioned in the cell, not allowing the study of those complex biological problems that require analysis of a large number of samples.

Integration of these nanoendoscopes with scanning probe techniques may overcome this limitation, potentially allowing automation and high-throughput analysis. In 2003, Osada and coworkers inserted atomic force microscope (AFM) tips into living cells to extract mRNAs (13). The mRNAs were analyzed with PCR techniques to validate the extraction protocol (14). More recently, Wickramasinghe's group optimized this method by coating AFM tips with platinum, which allowed extraction of the mRNA molecules through dielectrophoresis. Wichramasinghe's technology has been successfully combined with standard assay techniques to detect RNA molecules in breast cancer cells (15-16).

Manipulation and analysis of single cells is the next frontier in understanding processes that control the function and fate of cells. With the introduction of high-throughput sequencing it is now possible to obtain the collection of all active genes within a single cell, but the initial capture of genetic material of the cell still remains a major challenge. Furthermore, current methods for single-cell manipulation often can detect only one class of analytes.

SPECIFIC PATENTS AND PUBLICATIONS

Seger et al., "Voltage controlled nano-injection system for single-cell surgery," *Nanoscale* 4(19): 5843-5846 (2012), discloses developing a nanopipette as a label-free sensing platform (20-24) and an adaptation of ICM allowing the multi-component injection of single cells in culture (25).

Laforge et al., "Electrochemical attosyringe," *Proceedings of the National Academy of Sciences* 104(29): 11895-11900 (2007), discloses an electrochemical attosyringe based on a glass nanopipette to deliver a minute amount of liquid into a living cell via electrowetting (26).

Mirkin, et al., WO 2008/054488, published 8 May 2008 entitled "Electrochemical Attosyringe and Its Use as an Electrochemical Nanopump Driver," discloses a nanopipette filled with an organic solvent and an external voltage to drive aspiration and delivery of an aqueous solution.

Seger et al., US 2012/0225435, published Sep. 6, 2012, having at least one inventor in common with the present application and having the same assignee, entitled "Nanopipette apparatus for manipulating cells," discloses nanopipettes combined with an xyz controller and electronic control of a voltage differential in a bore of the nanopipette electroosmotically injecting material into a cell in a high-throughput manner and with minimal damage to the cell. Extraction of material from the cell and analysis of such material after ejection from the nanopipette is not disclosed in this application, nor is removal of biological materials in native form for further analysis.

Seger et al., "Voltage controlled nano-injection system for single-cell surgery," Nanoscale 4:19 2012 Sep. 28 pg 5843-6, contains a disclosure similar to the PG publication referenced above.

Pavel et al., US 20110131690, published Jun. 2, 2011, entitled "Scanning Ion Conductance Microscopy," discloses scanning ion conductance microscopy, and its use in the study of soft surfaces and interfaces, including those of cells and convoluted matrix structures. As disclosed there, scanning ion conductance microscopy (SICM) is a form of scanning probe microscopy (SPM) that allows the high resolution imaging of soft surfaces without any contact or force interaction whatsoever and in the normal liquid environment of the subject.

BRIEF SUMMARY OF THE INVENTION

The following brief summary is not intended to include all features and aspects of the present invention, nor does it imply that the invention must include all features and aspects discussed in this summary.

In certain aspects, the present invention pertains to a device comprising a nanopipette containing a tip and a first electrode in contact with a first electrolyte in or adjacent the interior of the nanopipette, and arranged to be connected to an amplifier input in a current detecting circuit and a second electrode in contact with a solution comprising a second electrolyte in the exterior of the nanopipette and cells, and arranged to be connected to the first electrode and the current detecting circuit wherein the first electrolyte and the second electrolyte permit ionic current to flow between the electrodes and through a nanoscale opening in the tip. In some aspects, the nanopipette is made of quartz, and may have a bore at the tip of 10-1000 nm, preferably on the order of 50-200 nm in diameter.

Further, the nanopipette device comprises an xyz controller attached to the nanopipette for effecting mechanical movements of the nanopipette in submicron x and y steps, and effecting movement of said nanopipette in a z direction towards or away from a cell, said xyz controller further having electronic controls for controlling said mechanical movements according to user defined control. In some aspects, the z direction of the nanopipette is controlled by a signal generated by the ionic current flow between the first and second electrodes. Such a device is coupled to a device that can image surfaces of cells with high resolution, e.g. a scanning ion conductance microscopy (SICM).

Such a device is referred to herein as a "nanopipette SICM" device, and may comprise a circuit for controlling a voltage, as further described in the above-mentioned US 2012/0225435.

In certain aspects of the present invention, the first electrode in the nanopipette device is silver tetrakis(4-chlorophenyl)borate (AgTBACI).

In certain aspects of the present invention, the first electrolyte solution is a hydrophobic liquid such as 1-2 dichlorethane containing an ionic material such as tetrahexylammonium tetrakis(4-chlorophenyl)borate (THATPBCl).

The present invention also comprises, in certain aspects, a method for controlling a nanopipette SICM device in order to carry out the extraction of pre-selected biological material from within the cytoplasm or an organelle of a single cell in order to analyze the biological material. This methodology is termed here "nanobiopsy." Unlike a conventional biopsy, the present nanobiopsy is conducted within a single cell; the cell is preferably a eukaryotic cell, preferably an animal cell that has been extracted from the host organism and placed on a sample stage for use with a microscope. The cell may be one which has been extracted by a conventional biopsy, or it may be taken ex vivo by other means, such as a blood draw, bone marrow aspiration, etc. The cell may be cultured ex vivo for a period of time prior to nanobiopsy. The material extracted can be obtained without relying on an affinity compound or chemical treatment. The material is obtained in its native state and without introducing any selection bias based on immunoreactivity, sequence identity or the like.

In certain aspects of the present invention, a nanopipette apparatus is controlled as follows:

1. The nanopipette is provided with a liquid organic solvent and an internal electrode that is connected to another electrode outside of the nanopipette, but in a solution (medium) contacting a cell to be analyzed.
2. The internal electrode is polarized with a positive bias (e.g. 200 mV) to prevent medium from flowing into the cell.
3. The nanopipette is guided to the cell surface by measuring ionic conductance, and, when the nanopipette is just above the cell surface it is rapidly lowered to pierce the cell. This step can be guided by optical microscopy or other microscopy that allows imaging of the cellular component of interest. For example, a mitochondrion is generally about 1-10 µM in length and can be seen in an optical microscope. The cell may be stained to identify visually a selected mitochondrion.
4. Once the nanopipette tip is inside the cell, the nanopipette bias is switched from positive to a negative bias (e.g. −500 mV or a range of −200 to −1000 mV) for a predetermined time, to cause influx of targeted biological material into the nanopipette. The "targeted intracellular content", i.e. biological material is targeted by physical location in the cell, and the nature of the molecules that are to be collected, e.g. genomic DNA, mitochnrial DNA, mRNA, rRNA, cytoplasmic proteins, nuclear proteins, lysomal proteins or membranes, polysaccharides, etc.
5. Step 4 is followed by a switch to a positive voltage of e.g. 200 mV or a range of 200 mV to 500 mV that stops the influx but does not allow efflux of the contents of the nanopipette.
6. The nanopipette is quickly raised, removed from the cell and surrounding medium, and moved to a transfer container, where the voltage is again switched to positive (e.g. +1V or a range of 500 to 1000 mV) to cause efflux of the aspirated contents into a sample container for analysis.

The sample container may contain a nucleic acid storage buffer, such as, e.g. a nuclease-free solution of PBS, or various buffers described e.g. in US 2012/0171685.

In certain aspects of the present invention, the aspirated contents from step 6 are analyzed to determine or identify a base sequence of DNA in the sample. This can be done by a variety of methods, including real-time PCR or next generation sequencing (NGS).

Thus the device described above may be characterized as a device for extracting intracellular content from a single cell, comprising: a nanopipette mounted on an xyz controller and containing a first electrode adapted for use with a first, hydrophobic electrolyte solution in the interior of the nanopipette; a second electrode outside of the nanopipette, arranged and adapted to contact a second, different electrolyte solution contacting the exterior of the cell; a current detecting circuit and a voltage control circuit, said current detecting circuit detecting ionic current between electrodes, and said voltage control circuit constructed to control a flow of liquid into and out of the nanopipette at predetermined times by reversing a voltage between the first electrode and the second electrode.

Various embodiments of the device may further be configured comprise wherein said xyz controller is attached to the nanopipette for effecting mechanical movements of the nanopipette in submicron x and y steps, and effecting movement of said nanopipette in a z direction towards or away from a cell, said xyz controller further having electronic controls for controlling said mechanical movements according to user defined control and said voltage control reverses voltage when said xyz controller has positioned the nanopipette tip within a cell. Various embodiments of the device may further be configured wherein the z direction of the nanopipette is controlled by a signal generated by the ionic current flow between the first and second electrodes. Various embodiments of the device may further be configured where the first electrode is silver tetrakis(4-chlorophenyl)borate (AgTBACl). Various embodiments of the device may further be configured wherein the first electrolyte solution comprises a hydrophobic liquid such as 1-2 dichlorethane and an ionic material on comprising tetrahexylammonium tetrakis(4-chlorophenyl)borate (THATPBCl). Various embodiments of the device may further be configured wherein the nanopipette is quartz.

The devices above may comprise a programmed instructions that operate the device according to steps comprising: (a) providing a first bias voltage to hold the first electrolye in the nanopipette; (b) providing a second, different bias voltage to cause influx of material from within the cell; and (c) providing a third, different bias voltage to cause efflux of fluid from the nanopipette.

Various embodiments of the device may further be configured to comprise a set of programmed instructions that operate the device in response to changes in ionic current sensed by the current detecting circuit.

In certain aspects of the present invention, the intracellular content from a cell, extracted in native form by the present method, comprises either organelles or nucleic acids. In some aspects, the extracted nucleic acids include genomic DNA, RNA (including mRNA and rRNA from a ribosome), or mitochondrial DNA. In other aspects, the organelle is a mitochondrion. In addition, one may extract portions of a cellular cytoplasm or vesicle containing proteins, small molecules, metabolites of cellular processes, etc.

In certain aspects, the present invention also pertains to a method for mechanically extracting intracellular content from a cell, comprising (a) preparing a solution comprising cells having a target intracellular content for extraction; (b) actuating a SICM nanopipette as described herein to approach a cell by sensing ionic current; (c) using the nanopipette to penetrate a cell surface; (d) adjusting the ionic current to generate a negative bias for a predetermined time and voltage in order to cause a controlled influx that extracts the target intracellular content into the nanopipette; and (e) further adjusting the ionic current to generate a positive bias in order to prevent the extracted contents from leaving the nanopipette and, further, to expel the contents of the nanopipette into a container for further analysis.

Various embodiments of the method may further comprise for extracting a targeted intracellular content from an individual cell, comprising: preparing a solution containing at least one cell having a target intracellular content for extraction; providing a nanopipette SICM device having an xyz controller, an internal electrode and an external electrode for creating a bias voltage, and further having a nanopipette containing a hydrophobic solution and having a tip; manipulating the nanopipette SICM device to approach said one cell by sensing a drop in ionic current through the tip.

Various embodiments of the method may further comprise generating a positive voltage between the interior electrode and the exterior electrode to prevent liquid from entering a hydrophobic solution in the nanopipette during insertion in to the cell; positioning the nanopipette to penetrate a predetermined cellular location and inserting it into the cell; adjusting the voltage in order to cause nanopipette influx and extract target intracellular content; further adjusting the voltage in order to prevent extracted target intracellular content from leaving the nanopipette; and further adjusting the voltage to cause an efflux of the extracted target intracellular content to a sample container.

Various embodiments of the method may further comprise wherein the extracted target intracellular content comprises nucleic acids, comprise DNA or RNA, and/or may comprise mitochondrial DNA.

Various embodiments of the method may further comprise steps wherein the voltages are one or more of (a) −100 to −1000 mV to cause influx of target intracellular content into the nanopipette; (b) 100-500 mV to stop influx and prevent efflux from the nanopipette; and (c) +0.5 to 2 V to cause efflux of the extracted target intracellular content. Various embodiments of the method may further comprise steps wherein the influx in step (a) lasts between 1 and 5 seconds.

Various embodiments of the method may further comprise steps wherein the efflux is into a sample container containing a nucleic acid storage buffer. Various embodiments of the method may further comprise steps wherein the extracted target intracellular content is DNA from a single mitochondrion and further comprising the step of determining a portion of the sequence of the mitochondrial DNA.

Various embodiments of the method may further comprise a method for extracting intracellular content from an individual cell, comprising: (a) providing a nanopipette having an xyz controller, an internal electrode and an external electrode for creating a bias voltage, and further having a nanopipette containing a tip for piercing a single cell; (b) manipulating the nanopipette device to cause nanopipette influx and extract target intracellular content of a cell; (c) further adjusting the voltage in order to prevent extracted target intracellular content from leaving the nanopipette; (d) further adjusting the voltage to cause an efflux of the extracted target intracellular content to a sample container; and (e) analyzing the extracted target intracellular content by one or both of (i) analyzing mRNA from the extracted target intracellular content; and (ii) analyzing one or more selected proteins from the extracted target intracellular content.

Various embodiments of the method may further comprise steps wherein said analyzing mRNA includes analysis of at least 500 pg of mRNA from the cell, or wherein the analyzing mRNA includes analyzing at least 90% of the mRNA sequences in the cell.

Various embodiments of the method may further comprise analyzing a protein comprises an ultra-sensitive assay, e.g. immunoassay, detecting a specific protein such as a proximity ligation method. The analyzing may comprise analyzing a protein species comprises analyzing at least one of EGFR, MKK1, ERK1/2, JAK, AP1/Jun, and STAT; distinguishing a phosphorylated protein from the same protein that is not phosphorylated; analyzing carried out multiple times on the same cell at different times; distinguishing a phosphorylated protein from the same protein that is not phosphorylated; and/or distinguishing a protein having post-translational modification from the same protein that is not so modified.

BRIEF DESCRIPTION OF THE DRAWINGS

FIG. 1A shows an automated approach of the nanopipette tip to the cell surface, where the nanopipette tip is below the surface of a liquid bathing the cell; FIG. 1B shows penetration of the tip into the cell cytosol followed by controlled aspiration of cytoplasmic material; FIG. 1C shows the retraction of the nanopipette; and FIG. 1D shows delivery of the biopsied material into a tube for analysis. The external electrode in the medium is not shown.

FIG. 9A shows alternative 3' exon usage in the gene PABPC1. Ensemble gene predictions are displayed at the bottom, where lines represent introns and rectangles represent exons. These gene predictions are on the reverse strand and are displayed in the 3' to 5' direction. Alternative 3' exon usage in the gene PABPC1 is seen in M3 and M7 vs M8. M8 shows coverage over the 3' region of the longer isoform, whereas M3 and M7 show coverage over the shorter isoform. FIG. 9B shows read coverage extends across the entire length of the gene MCCC2, demonstrating the feasibility of generating full length cDNA from transcripts isolated by nanobiopsy. The gene MCCC2 is displayed at the bottom in the 5' to 3' direction.

DETAILED DESCRIPTION OF THE PREFERRED EMBODIMENT

Definitions

Figure 1A:
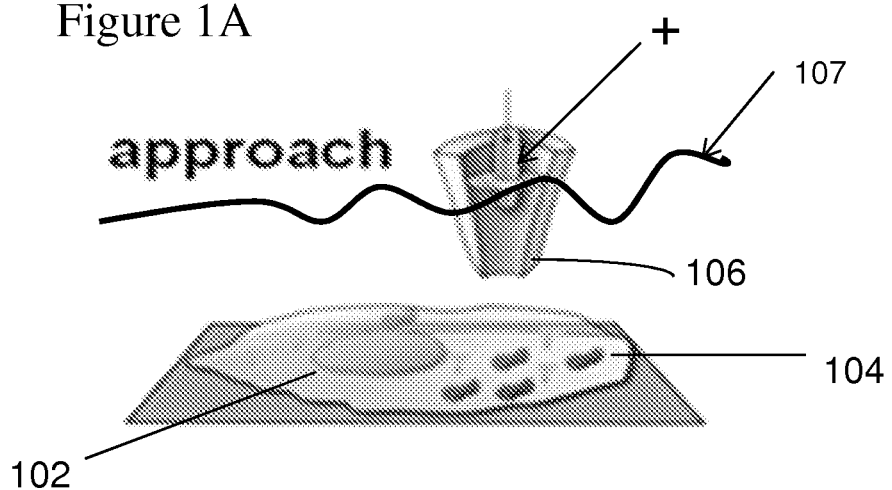
FIG. 1A-1D is a set of drawings showing single cell nanobiopsy and transfer of the contents of a single cell organelle or cytoplasm for post aspiration analysis.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "electrowetting" is used herein in its conventional sense to refer to the effect that employs an applied electric field to move liquid drops and films. It is used here to cause a cellular solution to flow into a nanopipette when a negative voltage is applied and to flow out when the bias is reversed. As an example, Laforge and coworkers exploited electrowetting in nanopipettes to inject fluorescent dyes into living cells in culture (26).

The term "ion conductance microscopy (ICM)" or "scanning ion conductance microscopy (SICM)" is used herein to refer to a scanning probe technique that has the ability to image living cells with high spatial (17) and temporal resolution (18). ICM relies on a glass nanopipette filled with an electrolyte solution biased to generate an ion flow through the nanopipette aperture. The nanopipette is then scanned over a surface, and changes in the magnitude of the measured ion current reflect changes in the topography of the sample studied (18-19). If the tip is scanned across the sample, an image can be rendered (28).

The term "nanopipette" is used herein in its conventional sense to refer to a hollow self-supporting, inert, non-biological structure with a conical tip opening (i.e. a nanopore) of nanoscale, i.e., 0.05 nm to about 500 nm, preferably about (+ or −20%) 50 nm. The hollow structure may be glass or quartz, and is suitable for holding inside of it, or on one side of the nanopore, a fluid which is passed through the nanopore opening. The interior of the nanopipette is selected or modified to minimize nonspecific binding of analyte. The interior is sized to allow insertion of an electrode that contacts solution in the nanopipette. Nanopipettes are preferably fabricated by laser pulling of glass or quartz capillary tubes. Nanopipettes have an inner diameter on the order of 10-100 nm, an outer diameter on the order of 200-800 nm, and a typical length of about 10 µm. These dimensions are sized to suit a particular application, and control of the nanopore size is an important consideration. A "multibarrelled nanopipette" is a nanopipette that has two or more parallel bores that typically share a common wall. The bores are co-axial, typically radially spaced, but may be concentric. They may be fabricated from multibore capillary tubes, which are commercially available.

The term "micromanipulator" or "xyz controller" refers to a mechanical device that moves in three dimensions, known as the x and y dimension, typically a flat surface, and the z direction, typically vertical. Xyz controllers are known for use in a variety of micro-scale applications, such as an atomic probe microscope; see, e.g. U.S. Pat. No. 5,394,741 to Kajimura et al., entitled "Atomic probe microscope," for further details on an exemplary xyz controller.

The term "current detecting circuit" or "circuit for controlling a voltage" refers to known electronic circuits and devices that include a controllable amplifier and a sensitive voltage and current detector. They may comprise any sensitive device for detecting changes in current on the order of 1-10 picoamperes, based on a baseline current of 10-10000 picoamperes and, further to change the voltage and/or current in response to such changes. The term further refers to a circuit that is time responsive and relatively temperature independent or allows for changes in temperature to be compensated for. It should have an input in a circuit where a known voltage is supplied. Sensitive detecting circuits are known, including voltage clamp amplifiers and transimpedance amplifiers.

The term nanopipette SICM device means a scanning ion microscopy device using as a probe a nanopipette. It has a control circuit that effectively sets internal bias voltages for holding, inputting and expelling fluid within, to, or from the bore of the nanopipette. The bias voltages are set by an internal electrode in an electrolyte solution within the bore of the nanopipette and an external electrode in a conductive solution external to the nanopipette, but in contact with the nanopipette during operation. The term "bias" voltage is used in a general sense, but preferably is a fixed DC voltage.

The term "ultra-sensitive assay" includes PLA, as defined below, and assays that can detect proteins and other cellular non-nucleic macromolecules, particularly proteins. Ultra-sensitive refers to the ability to obtain a meaningful result (protein modification and/or quantification) based on the contents of a single cell. This is particularly applicable to cytoplasmic and secreted proteins. Ultra-sensitive assays may detect as low as femtogram quantities of a specific protein.

Examples of an ultra-sensitive immunoassay include, "Wide range luminescent immunoassays," US 20130273667, "Ultra-sensitive detection of molecules or particles using beads or other capture objects," US 20120289428, and ultrasensitive enzymatic radioimmunoassay method, U.S. Pat. No. 4,289,748 A.

The term "post translation modification" refers to a protein that has been modified by covalent addition of functional groups or proteins, proteolytic cleavage of regulatory subunits or degradation of entire proteins. These modifications include phosphorylation, glycosylation, ubiquitination, nitrosylation, methylation, acetylation, lipidation and proteolysis and influence almost all aspects of normal cell biology and pathogenesis. A protein that has not been modified in this way may be referred to as a non-modified protein.

The term "PLA" means a proximity ligation assay as described herein, where antibodies bound to epitopes that are spatially in proximity within a distance that will allow oligonucleotides attached to the antibodies to interact. This oligonucleotide interaction enables a sensitive detection based on polynucleotide detection, such as PCR. Examples of PLA, for further clarity, are given He J, Evers D L, O'Leary T J. et al. Immunoliposome-PCR: a generic ultra-sensitive quantitative antigen detection system. J Nanobiotechnology. *J Nanobiotechnology.* 2012;10:26, and "Ultra-sensitive immunoassays, U.S. Pat. No. 6,878,515, to Ulf Landegren.

The term "EGFR" means "epidermal growth factor receptor," for example, human epidermal growth factor receptor, described further at Uniprot Q504U8 (Q504U8_HUMAN).

The term "MKK1" means MAP kinase skh1/pek1, for example, Uniprot Q02750 (MP2K1_HUMAN).

The term "ERK1/2" means extracellular signal-regulated kinase, for example Uniprot P27361 (MK03_HUMAN).

The term "JAK" means Janus kinase 2, for example Uniprot O60674 (JAK2_HUMAN).

The term "AP1/Jun" means the family of activator protein 1 (AP-1), which is a transcription factor which is a heterodimeric protein composed of proteins belonging to the c-Fos, c-Jun, ATF and JDP families. The AP-1 (activator protein-1) transcription factors, also known as JUN factors, are broadly acting factors regulating many inducible genetic responses. An example is PELI3, Uniprot Q8N2H9 (PELI3_HUMAN), which activate AP1/JUN and ELK1.

The term "STAT" means signal transducer and activator, which is a family of transcription latent transcription factors that reside in the cytoplasm until activated. The seven mammalian STATs bear a conserved tyrosine residue near the C-terminus that is phosphorylated by JAKs. An example is Uniprot P42226 (STAT6_HUMAN).

Overview

Disclosed herein are devices and methods for a system using a nanopipette integrated into a scanning ion conductance microscope (SICM) to extract intracellular content from a cell, including organelles and organelle content. This technology can be applied with single-cell sequencing techniques (32) to allow detailed studies of heterogeneity in living tissues with spatial and temporal information. Current methods for single-cell manipulation often can detect only one class of analytes, but the nanobiopsy platform described herein can be applied to genomics, proteomics, and metabolomics analysis (33). This technology can be implemented by a computer comprising programmed instructions and programmed instructions to carry out the present method that are embodied in a computer readable form.

Integrated Nanopipette SICM Device

Nanopipettes were fabricated as described in further detail below and integrated into a SICM set-up, which allows automated positioning of the nanopipette a few hundreds of nanometers above a cell (25). SICM devices have been previously devised for imaging the topography of soft non-conducting surfaces. See, e.g. Hansma, P. K., et al., *The Scanning Ion-Conductance Microscope*. Science, 1989. 243 (4891): p. 641-643. Such prior art devices use XYZ scanning, Z feedback and control logic (Z is considered to be the direction orthogonal to the surface being scanned).

Briefly, a general SICM configuration consists of a nanopipette back-filled with a hydrophobic electrolyte solution and immersed in an electrolytic bath. An electrode is placed in the nanopipette and a ground electrode is placed at some distance away in the bath. When a nanopipette is filled with an organic solution and immersed into an aqueous one, a liquid-liquid interface is formed at the nanopipette opening. If a voltage is then applied across this interface, a force is generated that can induce the aqueous solution to flow into/out of the nanopipette (28). The ionic current also acts as a feedback signal to precisely control the height of the nanopipette at a predefined distance above the surface of a cell.

In some embodiments, the tip of the nanopipette is fabricated or adjusted based upon the size of the target intracellular material to be extracted. Further, the tip is designed to be durable and sturdy enough to penetrate a cellular wall or membrane.

Additionally, features of this device may be incorporated into related devices for extracting an object from a single cell, or for measuring molecular binding within a single cell.

Intracellular Extraction

As seen in FIG. 1A-1D, the method for extracting intracellular content from a cell comprises using the nanopipette device described herein in the following steps:

1) Approaching the cell surface (FIG. 1A); the cell can be seen to have a nucleus 102 and mitochondria 104. This step is preferably carried out using a sensing circuit that detects the proximity of the nanopipette tip 106 to the surface of the cell. As described here, this can be done by measuring the changes in ionic current flowing through the nanopipette tip 106 as the tip is scanned along the sample surface containing the cell. The surface of the liquid bathing the cell is shown at 107. FIG. 1A shows that a small positive bias in the pipette prevents inflow.

Figure 1B:
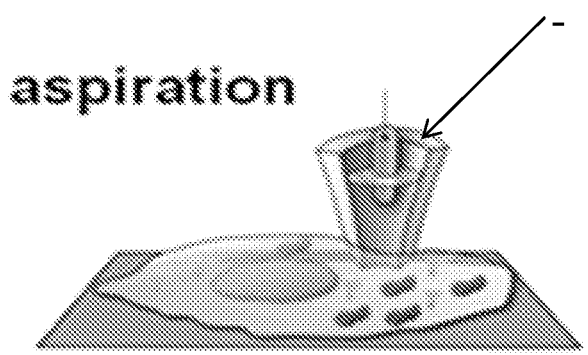

2) Penetrating the cell surface (FIG. 1B); here the organelle of interest has been located and the tip of the nanopipette positioned directly above it. It is then moved e.g. by an xyz manipulator rapidly downwardly so as to penetrate the outer cell membrane and penetrate the membrane of the organelle. The depth of penetration may be pre-programmed based on known cellular dimensions. For example, a human lymphocyte may range between 6-12 µm in diameter. A typical human cell is about 10 µm in diameter. Fibroblasts come in various shapes and sizes, as well as in an activated and unactivated form. Bacteria, for example, typically range in size from 0.5 to 1.5 µm. FIG. 1B show that a negative bias in the pipette is used to cause influx from within the cell.

3) Aspiration (extraction) of the target intracellular material (FIG. 1B); here the nanopipette bias voltage is switched to a negative potential so that the cellular material enters the nanopipette. When a dichloroethane(DCE)-filled nanopipette is immersed into an aqueous solution, a liquid-liquid interface is formed at the nanopore lumen due to the hydrophobic nature of DCE. The application of a voltage across this interface induces a change in the DCE surface tension. This effect, called electrowetting, causes the aqueous solution to flow in the nanopipette when a negative voltage is applied and to flow out when the bias is reversed. Other hydrophobic solvents may be used, such as those having a solubility in water of less than 0.5 g/110 g, e.g. as listed at http(colon-slash-slash) murov.info/orgsolvents.htm.

Figure 1C:
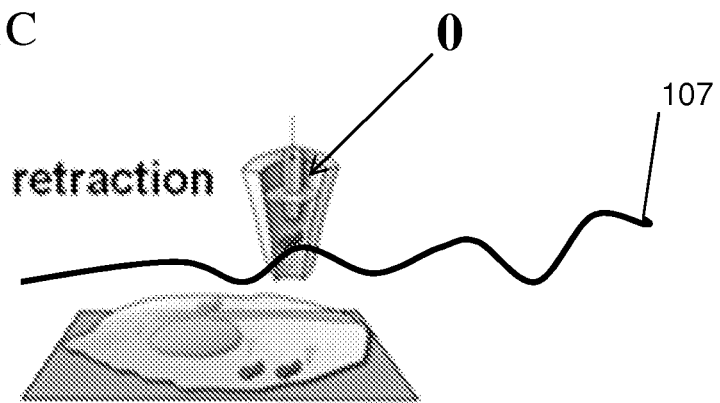
Figure 1D:
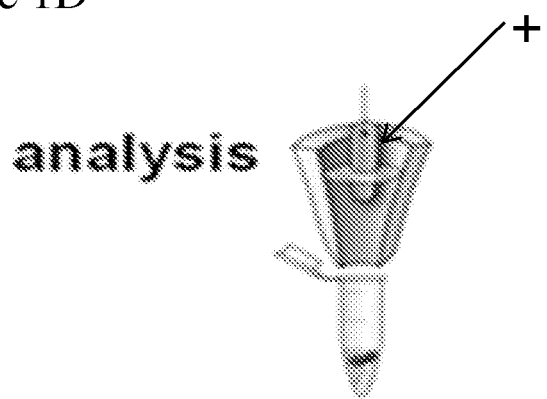

4) Retraction of the nanopipette (FIG. 1C); at this point, the nanopipette is biased to a holding state until clear of the liquid bathing the cell; FIG. 1C shows a holding potential in pipette to prevent outflow; and 5) Analysis of the extracted material (FIG. 1D). Here, the nanopipette is biased to positive state to expel the contents. FIG. 1D shows a strong positive bias in pipette to cause efflux into sample container.

Before use, the nanopipette is first filled with a hydrophobic liquid containing electrolyte and a coated wire electrode is placed in the electrolyte solution within the barrel of the nanopipette. To reiterate, the nanopipette tip is positioned over a cellular component of interest using either SICM or optical microscopy and the xyz controller capable of nanoscale movement. It is lowered into a solution surrounding the cell(s), preferably comprising a second electrolyte and growth medium. Here, the electrolyte within the barrel of the nanopipette is polarized with a positive bias to prevent unwanted solution from flowing into the barrel. This bias is created by a potential difference between the electrode in the nanopipette barrel and an electrode in the medium surrounding the cell. As described below, a voltage control circuit connects the electrodes and provides various bias voltages, preferably under computer control. This bias generates an ion current through the liquid-liquid interface which is used as the input into a feedback loop, such as provided by a feedback amplifier, or patch clamp amplifier arrangement.

The application of a voltage across this interface induces a change in the electrolyte surface tension through electrowetting. The electrowetting involves an interface between immiscible liquids, e.g. a hydrophobic and hydrophilic (aqueous) liquid.

Electrowetting may be carried out with other nonpolar liquids in the nanopipette bore. To identify these, one may refer to, e.g. Maillard et al., "Two liquids wetting and low hysteresis wetting on dielectric applications," Langmuir 25(11) 6162-6167 (2009).

Exemplary non-aqueous electrolytic solutions are: nitrobenzene solvent, containing 0.01 mol/L (or higher) tetrabutylammonium tetraphenylborate (TBA-TPB) electrolyte, or 1,2-dichloroethane solvent, containing 0.01 mol/L (or higher) TBA-TPB. Non-aqueous electrolytic solutions may also be formed with either solvent, but with TBA replaced by another tetra-alkylated ammonium cation, such as TEA, tetrapentylammonium, etc.

The TBA-TPB anion may similarly be exchanged for additionally functionalized phenylborates, such as tetrakis [3,5-bis(trifluoromethyl)phenyl]borate, or even for a simple halide, e.g. the iodide anion. The solvents and electrolytes listed here do not provide a comprehensive list of non-aqueous electrolytic solutions, but any combination of at least one of the exemplary solvents, at least one of the exemplary cations, and at least one of the exemplary anions may be used to create a non-aqueous electrolytic solution that may be suitable to support the electrowetting effect. See, Monroe et al., "Electrowetting devicees," WO 2008/142378.

Figure 2:
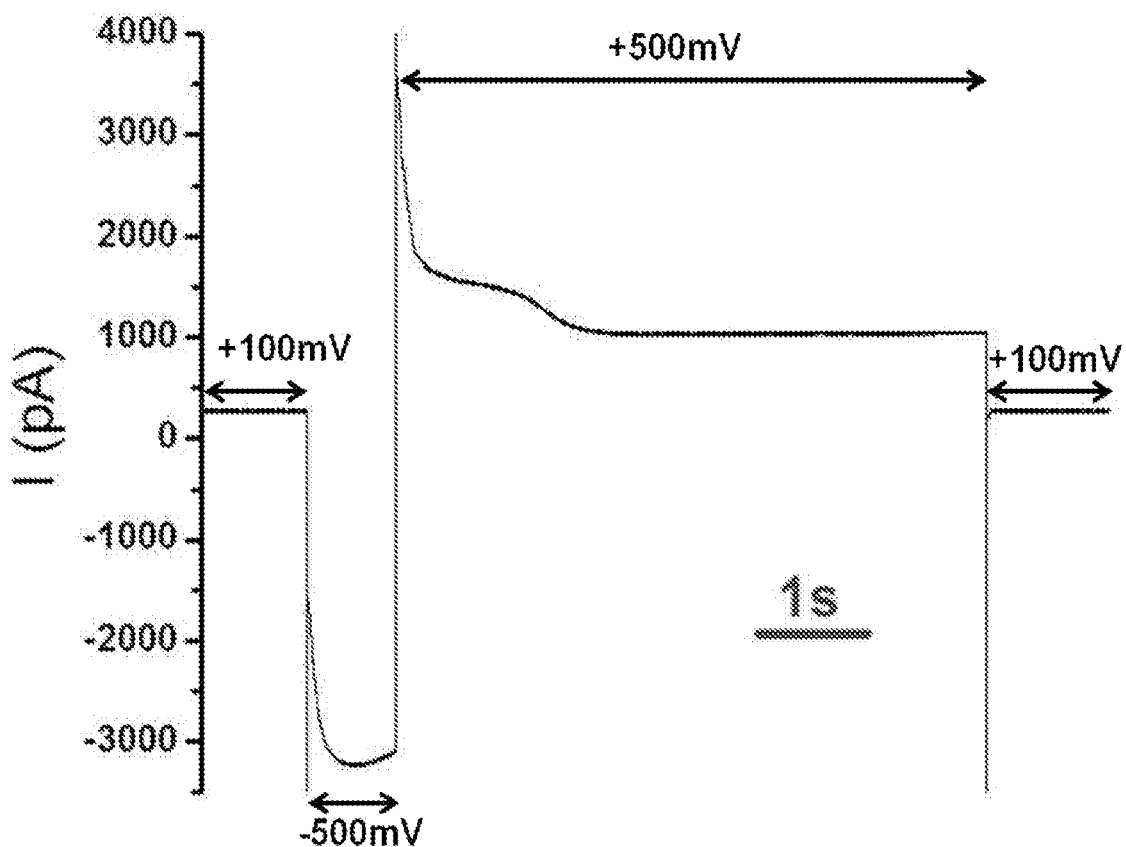
FIG. 2 is a trace showing results of electrowetting in a nanopipette. During the biopsy, the nanopipette is biased at +100 mV, then switched to −500 mV, and then to +500 mV. The curve obtained is the average of the results of 15 "aspiration-expulsion" cycles and shows changes in ionic current flow at different voltage states.

The nanopipette in the examples was filled with a solution of 1-2 dichlorethane (DCE) containing 10 mM tetrahexy-lammonium tetrakis(4-chlorophenyl)borate (THATPBCl). It was immersed in a PBS (phosphate buffered saline) bath. In FIG. 2, the nanopipette is biased at +100 mV to prevent any aqueous solution from flowing inside the nanopipette bore. By either manual or automatic operation, the nanopipette is lowered over an object to be biopsied, in this case a cell, until a threshold ionic current is detected. Once a specific threshold in ionic current is detected, the nanopipette is then further lowered at a high speed in order for penetration of the cell membrane to occur. In the exemplified device, custom written software directs the nanopipette towards the cell until the control circuit detects a 0.5% drop in the ionic current. This indicates proximity to the cell surface. At this point, the software stops the approach and quickly lowers the nanopipette by 1 uM to pierce the cell.

After piercing the cell membrane, the circuit is then switched to a negative bias, allowing for control over the aspiration of cellular contents within the cell cytoplasm into the nanopipette. Referring again to FIG. 2, when the bias is switched to −500 mV the measured ionic current increases due to the entry of the aqueous solution in the nanopipette barrel that has a higher conductance than the organic liquid initially filling the nanopipette barrel.

The bias is next switched back to a positive bias, stopping the influx into the nanopipette of cellular contents. The positive bias is strong enough to prevent the contents already aspirated from flowing out of the nanopipette. Again, FIG. 2 shows that when the voltage is switched to +500 mV, the aspirated aqueous solution is expelled resulting in a decrease in the measured ionic current, and providing a sample of intracellular content.

The cellular content extracted from the cell is then analyzed using known molecular biology techniques. The nano-biopsy platform allows sampling of organelles, including mitochondria, which has large implications for the study of diseases, such as cancers and neurodegenerative diseases.

In one embodiment of the present invention, a multibar-relled nanopipette is used with at least two electrodes in separate barrels. One barrel may be used for withdrawal of cellular contents, and another barrel may be used for injection of a material into the cell during the same operation. Multiple barrels may also be used for collecting different samples at different time points during a single injection.

Intracellular Content: Mitochondrial DNA

Mitochondrial DNA (mtDNA) was extracted from a single cell and mitochondrion and analyzed using molecular biology techniques. The DNA was extracted without any sort of chemical treatment being applied to the cell, and without lysing the cell.

mtDNA is the DNA found in the mitochondria of eukary-otes. Mitochondria are organelles responsible for generating the cell's supply of adenosine triphosphate (ATP), used as a source of energy for the cell. mtDNA may be single or, more commonly, double stranded and is usually circular or linear in shape. The mitochondrial genome consists of 16,596 nucleic acid base pair that encode 37 genes, 13 of which are for electron transport, 22 for tRNAs, and 2 for rRNAs. mtDNA analysis may be used to trace back a maternal lineage, since it is maternally inherited. It may be used to diagnose a genetic mitochondrial disease, See, for example, EP 1841884 A2, "Inherited mitochondrial dna mutations in cancer," which describes identifying in the subject a mis-sense mutation in a nucleic acid of Complex III, IV and/or V of the OXPHOS system. Such mutations that may be detected by an analysis carried out here therefore include, as described there, C5911T, G5913A, A5935G, G5949A, G5973A, G6081A, G6150A, T6124C, T6253C, G6261A, G6267A, G6285A, C6340T, G6480A, A6663G, G6924T, G7041A, T7080C, A7083G, A7158G, A7305C, A14769G, C8932T, and T7389C. The mutation may have the effect of inhibiting OXPHOS (Oxidative Phosphorylation) and increasing ROS (reactive oxygen species).

Nuclear DNA, found in the nucleus of the cell, contains more bases than mtDNA. However, since there are vastly more mitochondria within a cell there are many more copies of mtDNA than nuclear DNA, making mtDNA a particularly good target for analysis by the present method.

METHODS AND MATERIALS OF EXAMPLES

Nanopipette Fabrication

Nanopipettes were fabricated from quartz capillaries with filament with an outer diameter of 1.0 mm, inner diameter of 0.70 mm and length of 7.5 cm (Sutter Instrument Co., Item # QF100-70-7.5). Mean diameter=(106±16) nm (variation 15%).

SICM Setup

The Scanning Ion Conductance Microscope (SICM) consists of a low-noise amplifier (Axopatch 200B, Molecular Devices, Sunnyvale, Calif.) for nanopipette bias and current measurement, a micromanipulator (MP-285, Sutter Instrument Company, Novato, Calif.) for coarse control in the X, Y, and Z directions, a piezo actuator (Nano-cube, Physik Instrumente) for fine control in the X, Y, and Z directions, and a Field Programmable Gate Array (FPGA) (PCIe-7851R, National Instruments) for hardware control of the system. The system is controlled using custom coded software written in LabVIEW (1).

Cell Culture

BJ Human Fibroblasts were purchased from Stemgent Catalog #08-0027 and cultured in Stromal Cell Basal Medium (SCBM) (Lonza Cat. # CC-3204) with supplements (Lonza Cat. # CC-4181) with no phenol-red. HeLa cells (Cell Biolabs, INC., Catalog # AKR-213) expressing Green Fluorescent Protein were cultured in 70% DMEM medium supplemented with 10% fetal bovine serum, 0.1 mM Essential Amino Acids, 2 mM L-glutamine and 1% Pen-Strep as suggested from the supplier. All cells were cultured in 5% $CO_2$ at 37° C. Cells were plated on both ungridded and gridded plates (ibidi μ-Dish 35 mm, highGrid-500 uncoated, sterile) coated with 1% gelatin. Cells were plated with about $5 \times 10^4$ cells per dish.

THATPBCl Salt Synthesis

Tetrahexylammonium tetrakis(4-chlorophenyl)borate (THATPBCl) was synthesized by metathesis of tetrahexy-lammonium bromide (Aldrich, #263834) and potassium tetrakis(4-chlorophenyl)borate (Fluka, 60591). Both products were dissolved in a mixture of water/methanol (1:3) and recrystallized in ethanol (2).

Calcium Imaging

The invasiveness of the nanobiopsy platform was tested by monitoring [Ca$^{2+}$] before, during, and after the nanosurgical procedure. Human BJ fibroblasts were stained with 5 μM Fluo-4AM(Invitrogen) in medium, described in cell culture section above, prior to experimentation. Cells were then incubated at 37° C. for 30 minutes. Cells were washed twice with growth media.

Molecular Biology Techniques

Real-time qPCR Master Mix—SYBR Advantage qPCR Premix using SYBR Green I (Cat. No. 697676) was used following manufacturer recommendations.

iScript™ cDNA Synthesis Kit (Cat. Nos. 639505 & 639506) was used following manufacturer recommendations.

PCR Primers: HeLa-GFP

```
                                        (SEQ ID NO: 1)
    Reverse primer:    GCGCCGAGGTGAAGTTCGAGG (SEQ ID NO: 2)
    Forward Primer:    GCCGTCGCCGATGGGGGTGTT
```

Primer pair used to perform amplification on mitochondrial DNA, 30 cycles
Primer: 3,968 base pairs Gel Electrophoresis Ran in 2% Gel (2 g agarose in 100 ml TAE buffer)
Conditions: 95 Volts for 30 minutes Visualization of the Mitochondria Mitochondria were labeled with MitoTracker Green FM (Invitrogen) (excitation wavelength 490 nm, emission wavelength 516 nm). MitoTracker Green was dissolved in dimethylsulfoxide (DMSO) at a concentration of 1 mM and stored in −20°C Adherent fibroblast cells were stained with a diluted solution of 1 mM MitoTracker Green with a final concentration of 500 nM in medium. Cells were placed in 37° C. incubation for 30 minutes and washed twice. 1 mL of medium was then added to cells for experimental work. Only the mitochondria seemed to be noticeably stained when the petri dish was placed under a fluorescent lamp.

Nanopipette Device and Method for Subcellular Analysis of Proteins and Proteomics In addition to the above applications, the present instrumentation can be used for the detection and quantification of specific protein species and protein interactions within a single cell. This application uses a nanopipette with a 50 nm pore at is tip that is able to retrieve and deliver small samples (15 picoliters (~1% of the total cell). of cytoplasm from an individual cell, as described above. The nanopipette is integrated with scanning feedback technology to position the tip for single-cell resolution, as described above. By monitoring the ionic current at the nanopipette tip, the precise position of the nanopipette can be determined and controlled within ~200 nm of the cell membrane. After initial positioning above the cell, if one wants to sample cellular content, the nanopipette is inserted into the cell at a controlled speed, angle and depth. The nanopipette is then quickly (100 μm/s) lowered 1 μm, penetrating the cell membrane. Once inserted, the nanopipette can be used to inject or aspirate small amounts of cell content.

The nanopipette targets an individual living cell using scanning ion conductance microscopy, allowing the user to monitor the molecular biology of a single cell with temporal resolution. To analyze the changes in gene expression in single cells, one may employ the described, highly efficient methods for nucleic acid amplification and sequencing to allow for multiple measurements of the transcriptome in a single cell (Tariq M A, Kim H J, Jejelowo O, Pourmand N. Whole-transcriptome RNAseq analysis from minute amount of total RNA. Nucleic Acids Res 2011;39:e120.)

An important feature of the present method is a multiplexed proximity ligand assay (PLA). This is further described in, e.g. Fredriksson S, Gullberg M, Jarvius J et al. Protein detection using proximity-dependent DNA ligation assays. Nat Biotechnol 2002;20:473-7; Soderberg O, Gullberg M, Jarvius M et al. Direct observation of individual endogenous protein complexes in situ by proximity ligation. Nat Methods2006; 3:995-1000; Gullberg M, Gustafsdottir S M, Schallmeiner E et al. Cytokine detection by antibody-based proximity ligation. Proc Natl Acad SciUSA2004;101: 8420-4.; Bjarnegard M, Enge M, Norlin J et al. Endothelium-specific ablation of PDGFB leads to pericyte loss and glomerular, cardiac and placental abnormalities.Development 2004; 131:1847-57; Gustafsdottir S M, Nordengrahn A, Fredriksson S et al. Detection of individual microbial pathogens by proximity ligation. Clin Chem 2006; 52:1152-60; Fredriksson S, Horecka J, Brustugun O T et al. Multiplexed proximity ligation assays to profile putative plasma biomarkers relevant to pancreatic and ovarian cancer. Clin Chem 2008; 54: 582-9; and Blokzijl A, Friedman M, Ponte F & Landegren U Profiling protein expression and interactions: proximity ligation as a tool for personalized medicine. (Review) JInternMed 2010; 268:232-245.

It is important that the protein analysis be sensitive enough to measure multiple protein reactions in the same cell. PLA employs hybrid antibodies fused to oligonucleotides. Antibody-antigen binding is detected using qPCR providing a highly sensitive quantitative measure of protein levels. Various embodiments of the PLA are described further in Landegren U.S. Pat. No. 6,878,515, "Ultrasensitive immunoassays."

For example, one may use an established cell signaling pathway involved in cancer, the epidermal growth factor receptor (EGFR). It is known that when epidermal growth factor (EGF) binds to EGFR that a cascade of protein kinase pathways are activated in cancer cells that cause changes in gene expression that affect cell proliferation. As a proof of principle, a multiplexed PLA assay is therefore to measure a number of the protein phosphorylation events mediating EGF stimulation of gene expression in the triple negative breast cancer (TNBC) line MDA-MB-231. These cells have been extensively employed to study EGFR signaling and we have already begun to use the nanopipette to study gene expression in single MDA-MB-231cells.

The multiplexed EGFR PLA is integrated into the present nanopipette instrumentation and sensitivity of the PLA allows one to measure kinase activation pathways before and after EGF stimulation in the same cell. One may further integrate the nanopipette single cell PLA and whole transcriptome analysis (WTA) in measuring EGF signaling in the same cell over time. This provides a novel nanopipette technology capable of simultaneous protein post-translational and genomic readouts in single cancer cells over time.

EXAMPLES

Example 1

Nanobiopsy Platform Setup

Quartz nanopipettes with pore diameters of 115±15 nm (images not shown) were fabricated using a conventional laser-puller (P2000, Sutter Instruments) and filled with a solution of 1-2 dichlorethane (DCE) containing 10 mM tetrahexylammonium tetrakis(4-chlorophenyl)borate (THATPBCl).

To adapt the SICM as a single-cell biopsy platform, the nanopipette was filled with a 10 mM THATPBCl solution in DCE and fitted with a silver wire coated with silver tetrakis (4-chlorophenyl)borate (AgTBACl) in the barrel of the nanopipette. When a DCE-filled nanopipette is immersed into an aqueous solution a liquid-liquid interface is formed at the nanopore lumen due to the hydrophobic nature of DCE. The application of a voltage across this interface induces a change in the DCE surface tension. The application of a voltage across the interface between the hydrophobic liquid in the nanopipette and the electrolyte solution external to the nanopipette induces a change in the hydrophobic liquid surface tension. This electrowetting effect causes aqueous solution to flow into the nanopipette when a negative voltage is applied, and out of the nanopipette when the voltage bias is reversed.

The filled nanopipette was immersed into a petri dish filled with growth medium where cells were cultured. While in cell culture medium, the nanopipette is polarized with a positive bias to prevent medium from flowing into the barrel. This bias generates an ion current through the liquid-liquid interface which is used as the input into a feedback loop. The custom-written software directs the nanopipette toward the cell until it detects a 0.5% drop in the ionic current. At this point the software tells the xyz controller to stop the approach and quickly lower the nanopipette by 1 μm at a high speed (100 μm/s) to pierce the cell membrane, inserting the nanopipette tip into the cell cytoplasm.

Figure 3:
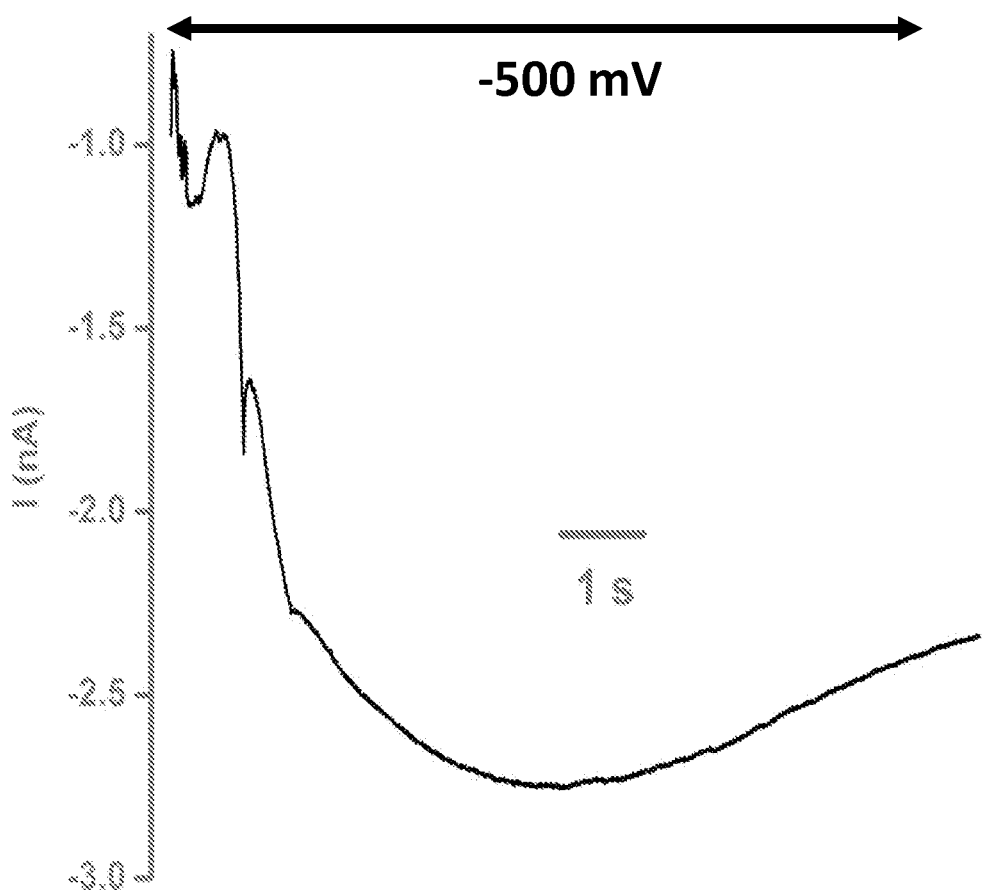
FIG. 3 is a trace showing chronoamperometry during single cell nanobiopsy. The nanopipette is biased at +100 mV to prevent any aqueous solution from entering the nanopipette. When the bias is switched to −500 mV, the ion current increases due to the entry of the cell cytoplasm in the nanopipette barrel.

At this stage the nanopipette bias is switched by the software to −500 mV for 5 seconds, which causes the controlled influx of cell cytoplasm into the nanopipette (FIG. 3).

Then the bias is switched by the software to 200 mV, a voltage sufficient to stop the influx but not to start the efflux of aspirated contents. The nanopipette is then quickly raised by the software, and the aspirated content is transferred by xyz control into a 5 uL droplet of RNase-free $H_2O$ by application of +1 V for 2 minutes (again under software control) and kept at 4° C.

Example 2

Biopsy of Green Fluorescent Protein Transcripts

Figure 4:
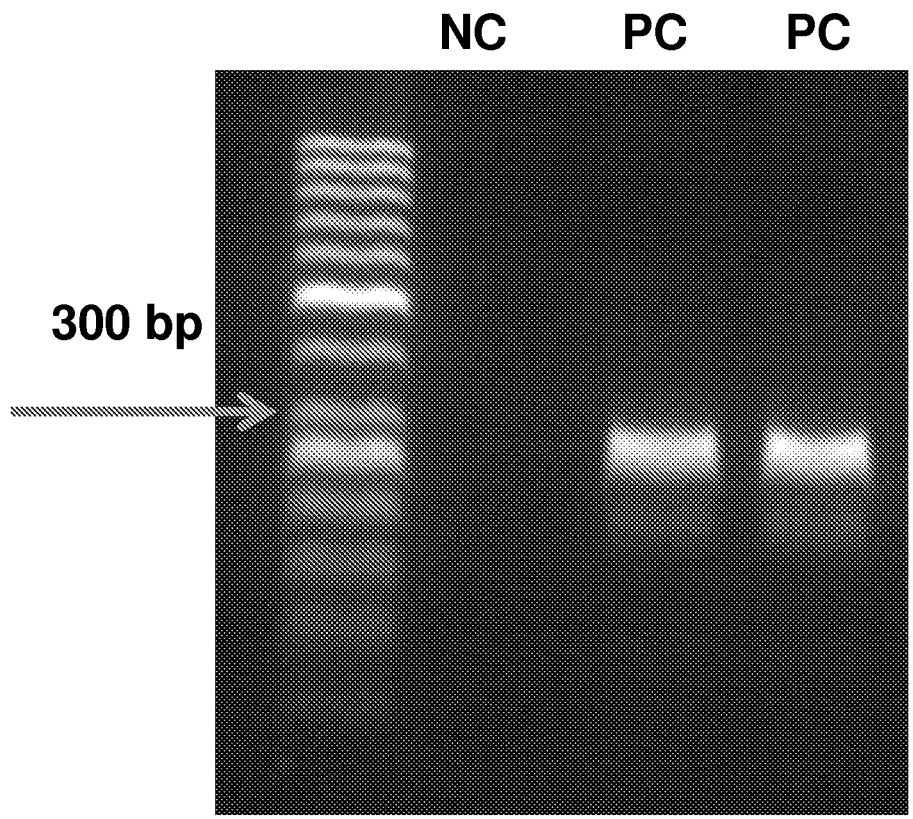
FIG. 4 is an image of a gel stained with SYBR® gold for fragment size determination (at expected size of ~250 base pairs) and polymerase chain reaction (PCR) amplification, following cDNA synthesis, for the GFP gene in GFP-HeLa cells (PC, positive control, ran in duplicate) and in human BJ fibroblasts (NC, negative control).
Figure 5:
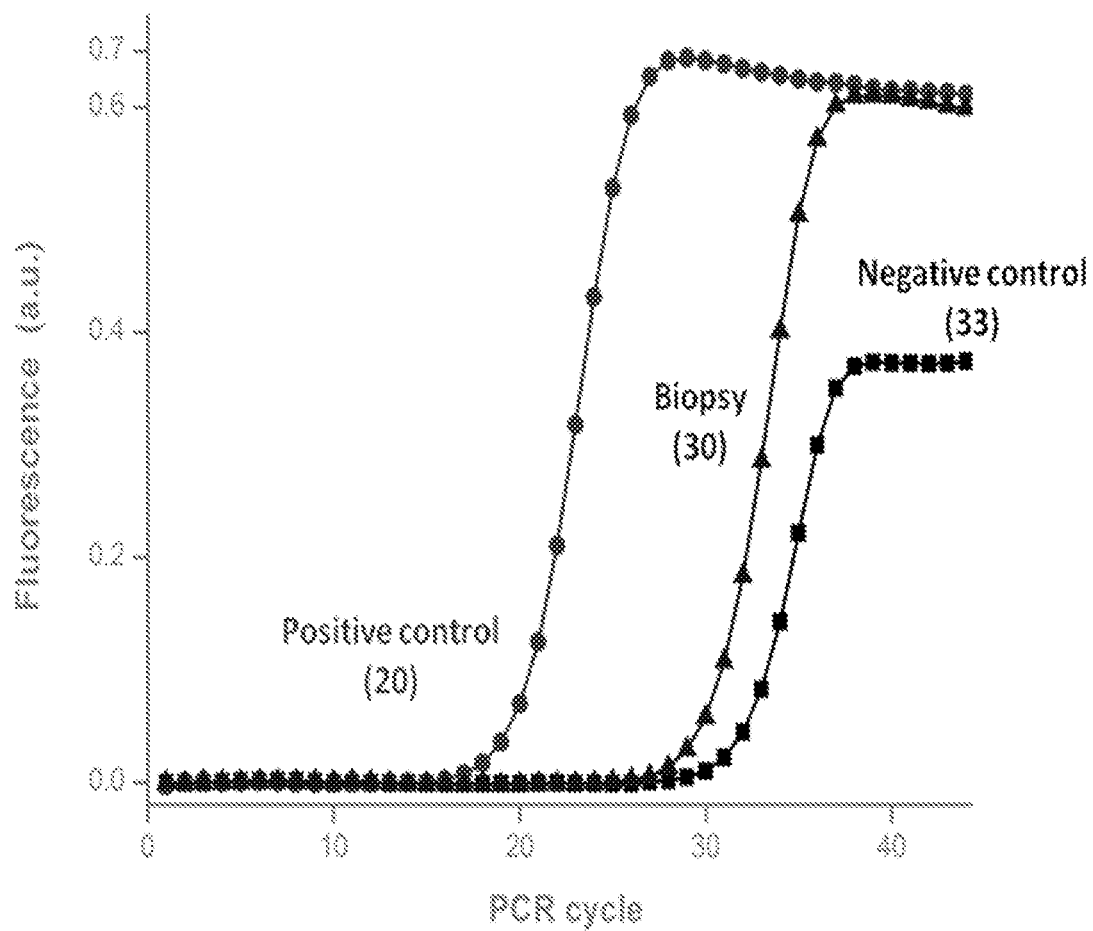
FIG. 5 is a line graph showing post biopsy analysis via qPCR targeting GFP RNA from HeLa cells showing a positive control of total RNA from a ~1,000 cells lysate (quantification cycle, Cq 20), a biopsy from a single cell (quantification cycle Cq 30), and water as a negative control (quantification cycle Cq 33).

We performed biopsies on HeLa cells expressing Green Fluorescent Protein (GFP) and used PCR methods to validate the success of the protocol by targeting selective amplification of GFP transcripts (FIG. 4). We performed cDNA synthesis on the content aspirated from within a single cell using iScript™ cDNA Synthesis Kit (BioRad). This process reverse-transcribed all the RNA present in the biopsy into cDNA. Real time-PCR is then performed on the cDNA to confirm the presence of GFP transcripts. In a real time-PCR experiment the fluorescence remains at background levels (cycles 1-18, FIG. 5) until enough amplified product accumulates to yield a detectable fluorescence signal. The cycle number at which this occurs is called the quantification cycle, or $C_q$. A difference of X in $C_q$ values of two reactions reflects a $2^X$ difference in amount of starting material.

Figure 6:
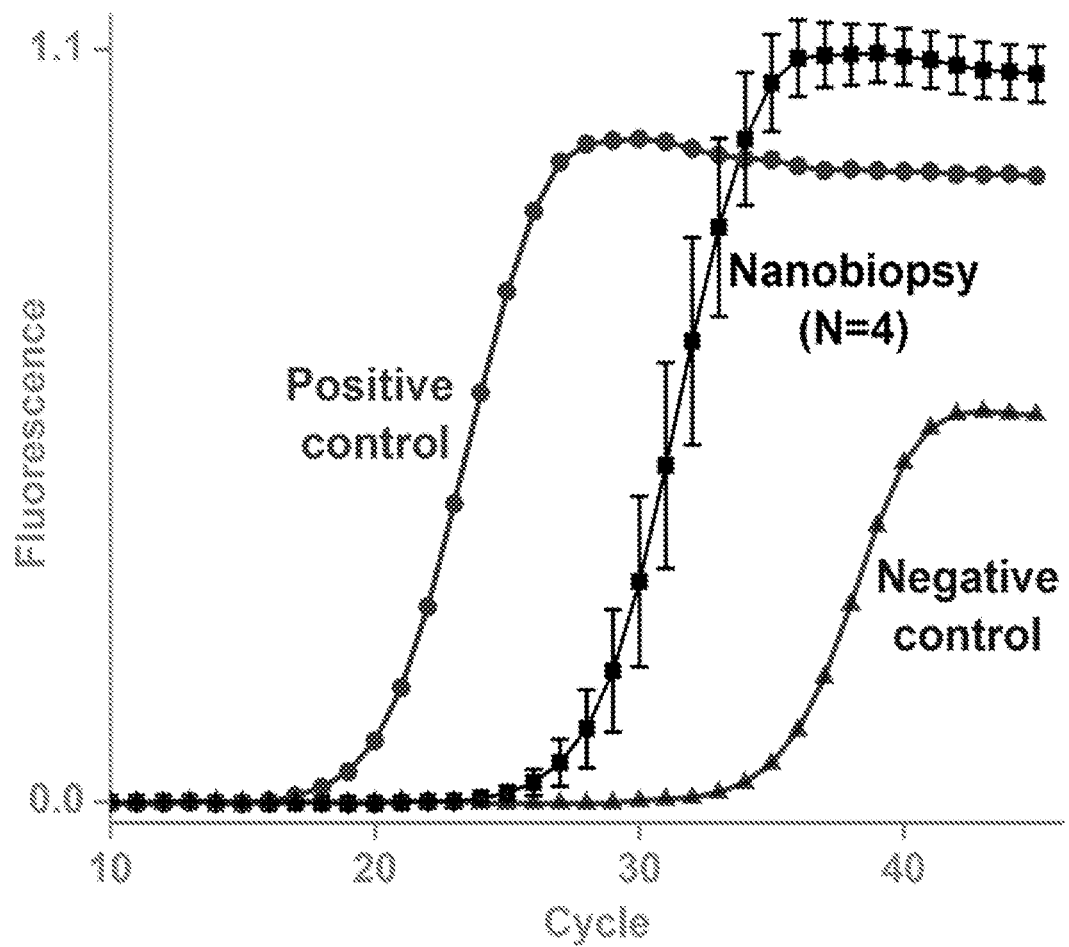
FIG. 6 is a line graph showing positive control (circles) consists of total RNA extracted from a lysate of ~1000 GFP-HeLa cells. The nanobiopsy (boxes) represents qPCR starting with the contents of a standard nanobiopsy of a single cell. The negative control (triangles) represents five samples, four nanobiopsy samples following our standard protocol without the application of ~500 mV after cell penetration (thus lacking the aspiration step), while the fifth sample used water as the starting material. The 4 samples of no applied voltage, and the sample with water all resulted in negative amplification compared to our nanobiopsy samples and positive control.

Real-time PCR amplification plots show a $C_q$ value of 20 for the positive control, where total RNA from a HeLa-GFP cell lysate was spiked in the cDNA synthesis reaction, 30 when the input RNA was the biopsied content and of 33 for the negative control when no RNA was added for the cDNA synthesis. As positive control we used total RNA extracted from ~1000 HeLa-GFP cells. The difference in $C_q$ values from the PC and biopsied sample was 10, which corresponds to a 1024 ($2^{10}$) fold difference in input material. We can thus conclude that the amplification plots are consistent with amounts of RNA extracted from within a single cell. The real time PCR protocols rely on a fluorescent dye (Sybr gold) which turns fluorescent when it intercalates double stranded DNA. The fluorescence increase in the negative control is caused by the formation of primer dimers. We diligently studied the reproducibility of the nanobiopsy protocols. Individual cells are known to have different gene expression patterns, and we thus tested the reproducibility of the nanobiopsy protocols by performing aspiration in a solution containing the lysate of ~1000 GFP HeLa cells. Post aspiration analysis via qPCR (FIG. 6) confirmed the high reproducibility of the nanobiopsy protocols.

Figure 7:
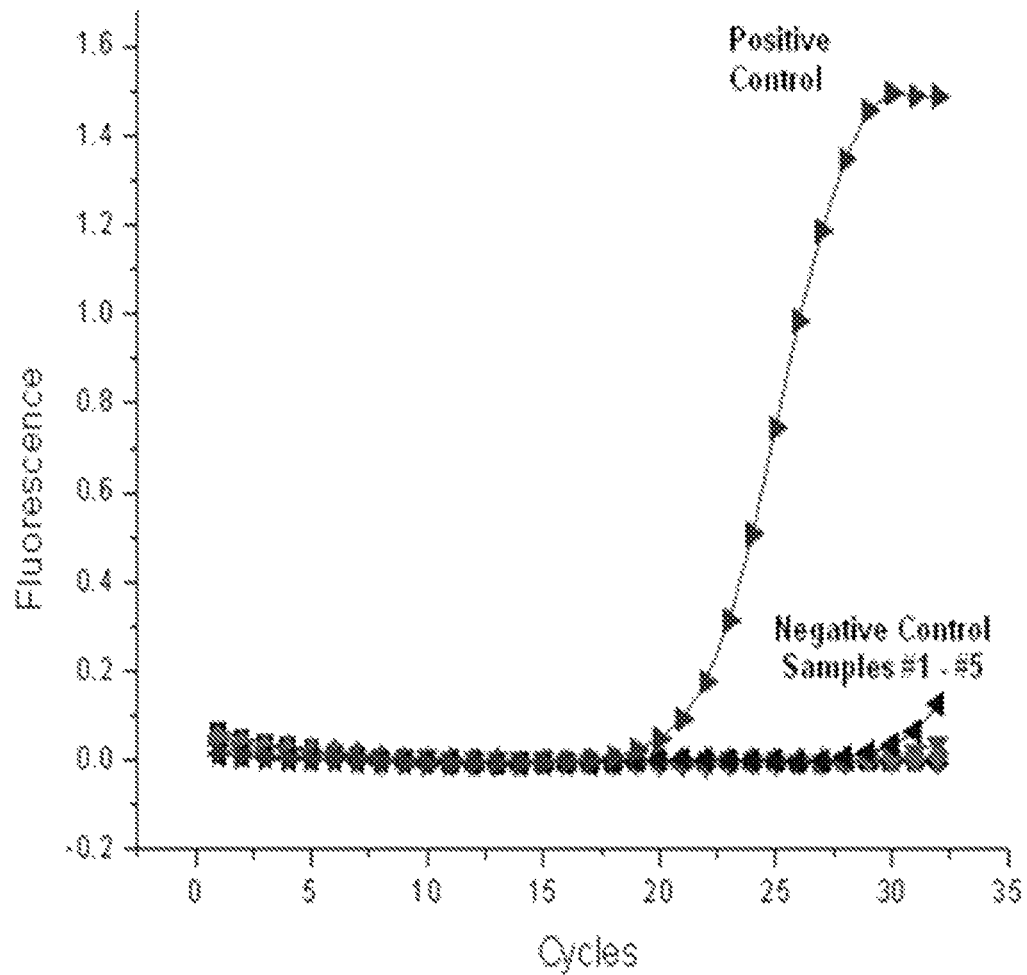
FIG. 7 is a line graph showing post biopsy analysis of a positive control and 5 negative control samples (samples #1-#5) via qPCR.

The biopsy relies on the voltage controlled aspiration of genetic material and not on physisorption on the nanopipette side walls. No amplification is observed when no voltage is applied to the nanopipette after insertion into the cell and when aspiration is performed in the bulk solution (FIG. 7). This is the key element that differentiates the nanobiopsy technology from AFM based platforms. Both Wickramasinghe's and Osada's groups have used AFM probes to extract RNA from cells in culture, either based on physisorption or hybridization of complementary RNA immobilized onto the probe (14-15). By contrast, the hollow nature of nanopipette probes allows fluid aspiration, thus not limiting its application to RNA extraction.

Example 3

Biopsy of Human BJ Fibroblast Mitochondria

Figure 8:
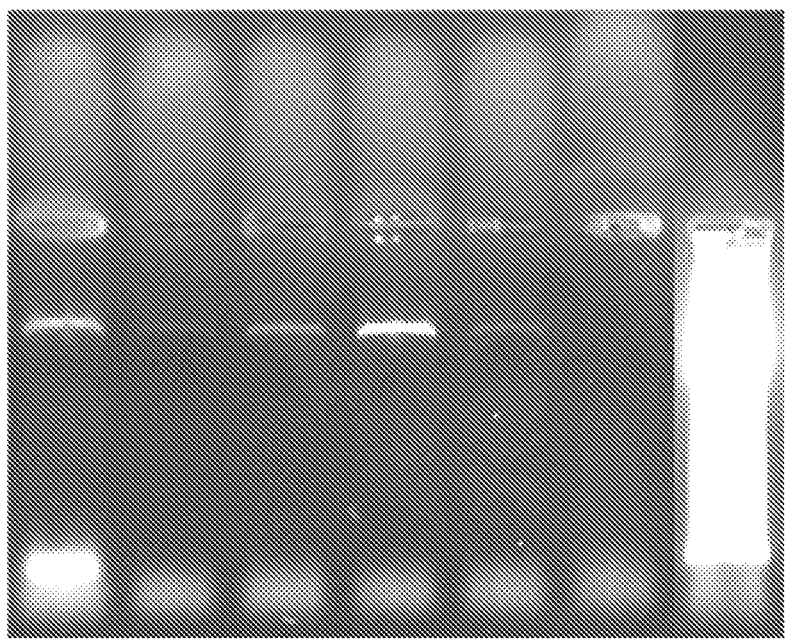
FIG. 8 is an image of a gel stained with Sybr gold for fragment size determination (at expected size of ~7000 base pairs) and polymerase chain reaction (PCR) amplification of mitochondrial DNA. Lanes 1-5, mitochondria biopsy on 5 individual human BJ fibroblast cells. Samples Lane 6 is the negative control where no biopsy was performed (no input DNA), and lane 7 is the positive control (mitochondrial PCR product as input material).

The nanobiopsy platform is by no means limited to RNA extraction from single cells but it can be employed to sampling of cellular organelles as well. Human BJ fibroblasts (skin fibroblast cells, ATCC CRL 2522) were stained using mitotracker (Invitrogen) (data not shown), a fluorescent label for mitochondria. The nanopipette was placed above a region with an abundance of mitochondria, and a biopsy was performed with the same protocol described before (data not shown). Fluorescence within the tip of the nanopipette indicates the successful aspiration of mitochondria (data not shown). PCR analysis of the biopsied mitochondria was used to confirm the presence of mitochondrial DNA. The mitochondrial DNA was amplified using primers specific to the mitochondrial genome, and gel electrophoresis of the amplified mitochondrial DNA shows that all 5 samples taken show bands at the correct length for human mitochondrial DNA (FIG. 8).

Example 4

Minimal Invasiveness of the Nanopipette

The modulation of cytosolic concentration of $Ca^{2+}$ is considered to be an indicator of mechanical stress caused by insertion of foreign objects (11, 30-31). To demonstrate the low invasiveness of the single-cell biopsy platform, we measured intracellular $[Ca^{2+}]$ before, during, and after the nanobiopsy (data not shown). Human BJ fibroblast cells were labeled with Fluo4 AM (data not shown). Optical micrographs confirm the minimally invasive procedure which generates a barely detectable $Ca^{2+}$ influx during nanobiopsy. The cell fully recovers within 5 seconds post aspiration, reaching [Ca$^{2+}$] matching pre-aspiration level.

Example 5

Nanobiopsy to Analyze Endogenous mRNA Expression

Electrowetting in Nanopipettes

Nanopipettes were fabricated from quartz capillaries (Sutter Instrument, Novato, Calif.) using a P-2000 laser puller (Sutter Instrument, Novato, Calif.). Mean diameter= (106±16) nm Quartz nanopipettes were filled with a solution of 1-2 dichlorethane (DCE) containing 10 mM tetrahexylammonium tetrakis(4-chlorophenyl)borate (THATPBCl). A silver wire coated with silver tetrakis(4-chlorophenyl)borate (AgTBACl) was then inserted into the barrel of the nanopipette, while a Ag/AgCl wire was immersed in the bath solution acting as a reference/counter electrode.

SICM Setup

The scanning ion conductance microscope (SICM) consists of a Axopatch 200B low-noise amplifier (Molecular Devices, Sunnyvale, Calif.) for nanopipette bias and current measurement, a MP-285 micromanipulator (Sutter Instrument, Novato, Calif.) for coarse control in the X, Y, and Z directions, a Nano-cube piezo actuator (Physik Instrumente, Irvine, Calif.) for fine control in the X, Y, and Z directions, and a PCIe-7851R Field Programmable Gate Array (FPGA) (National Instruments) for hardware control of the system. The system is operated using custom coded software written in LabVIEW8.

Cell Culture

BJ Human Fibroblasts were purchased from Stemgent and cultured in Stromal Cell Basal Medium (SCBM) (Lonza, Alpharetta, Ga.) with supplements (Lonza, Alpharetta, Ga.) with no phenol-red. HeLa cells (Cell Biolabs, San Diego, Calif.) expressing Green Fluorescent Protein were cultured in 70% DMEM medium supplemented with 10% fetal bovine serum, 0.1 mM essential amino acids, 2 mM L-glutamine and 1% Pen-Strep as suggested from the supplier. All cells were cultured in 5% CO2 at 37° C. Cells were plated on both ungridded and gridded plates (ibidi μ-Dish35 mm, highGrid-500 uncoated, sterile) coated with 1% gelatin. Cells were plated at about 5×104 cells per dish.

cDNA Synthesize and qPCR cDNA was synthesized from total RNA nanobiopsied from cells using iScript™ cDNA Synthesis Kit (BioRad, Hercules, Calif.) following manufacturer recommendations. Quantitative PCR (qPCR) was used to confirm the success of the nanobiopsy protocols using Clontech's Advantage qPCR Premix SYBR Green I Master Mix (Clontech, Mountain View, Calif.) following manufacturer recommendations. PCR primers: HeLa-GFP, Reverse primer: GCGCCGAGGTGAAGTTCGAGG (SEQ ID NO: 1), Forward Primer: GCCGTCGCCGATGGGGGTGTT (SEQ ID NO: 2) were used to amplify the aspirated mitochondrial DNA to amplify 3968 base pairs visualized by gel electrophoresis.

cDNA Synthesis and RNA Sequencing

Aspirated RNA samples were processed to cDNA using the Ovation® RNA-Seq system (NuGEN Technologies, San Carlos, Calif.). The cDNA was prepared for individual aspiration for library preparation. The quality and quantity of single-cell cDNA were evaluated using the Agilent Bioanalyzer 2100 DNA High Sensitivity chip (Agilent, Palo Alto, Calif.).

For paired-end whole transcriptome library preparation, ~0.5-1.0 μg cDNA of each sample was sheared to a size ranging between 200-300 bp using the Covaris-S2 sonicator (Covaris, Woburn, Mass.) according to the manufacturer's recommended protocols. Fragmented cDNA samples were used for the preparation of RNA-Seq libraries using TruSeq v1 Multiplex Sample Preparation kit (Illumina, San Diego, Calif.). Briefly, cDNA fragments were end repaired, dA-tailed and ligated to multiplex adapters according to manufacturer's instructions. After ligation, DNA fragments smaller than 150 bp were removed with AmPure XP beads (Beckman Coulter Genomics, Danvers, Mass.). The purified adapter ligated products were enriched using polymerase chain reaction (14 cycles). The final amplified libraries were resolved on 2.0% agarose gel and size-selected in the range of 350-380 bp using Caliper XT system (PerkinElmer, Waltham, Mass.). The final RNA-Seq libraries were quantitated using the Agilent bioanalyzer 2100 and pooled together in equal concentration for sequencing. The pooled multiplexed libraries were sequenced, generated 2×150 by paired-end reads on MiSeq (Illumina, San Diego, Calif.).

Mitochondrial DNA Amplification and Sequencing

Aspirated mitochondrial DNA was amplified by long-range PCR using a pair of primers; forward TCA TTT TTA TTG CCA CAA CTA ACC TCC TCG GAC TC (SEQ ID NO: 3) and reverse CGT GAT GTC TTA TTT AAG GGG AAC GTG TGG GCT AT (SEQ ID NO: 4) to generate a ~8K bp fragment. The aspirated mitochondrial genomes were amplified using long and accurate polymerase chain reaction (LA-PCR) LA PCR Kit Ver. 2.1 (Takara Bio). The mitochondrial genome amplification was carried out in a 25 μL reaction mixture containing aspirated template DNA, 2.5 L 10× Epicenter's boost, 2.5, μL 10× LA PCR buffer II (Mg2+ plus), 4.0 μL dNTP (2.5 mM), 1.25 μL of each primer (10 μM), 0.125 μL of LA Taq DNA Polymerase, and 11.4 μL sterile distilled water. Thermocycler conditions were 95° C. for 2 minutes, followed by 30 cycles, each consisting of 94° C. for 15 seconds then 68° C. for 8 minutes, and a final extension at 68° C. for 13 minutes. The mitochondrial amplicons were sheared by Covaris S2 system resulting in 300-400 bp fragments that were subjected to automated Illumina multiplex paired end library preparation on robot. A unique index sequence was used for each mitochondrial sample and sequenced in single Illumina HiSeq 2000 lane.

Bioinformatics Methods

Short reads from mitochondrial experiments were preprocessed to trim sequencing adapters from the 3' ends of reads. Mitochondrial reads were aligned to the revised Cambridge Mitochondrial Reference Sequence using a nonspliced aligner. Heteroplasmic variants between 5% and 99% were reported. Short reads from RNA-sequencing experiments were preprocessed to trim sequencing adapters from the 3' ends of reads. Ten bases from the 5' end of RNA-seq reads to remove biases introduced during second strand synthesis of cDNA. RNA-seq reads were aligned to the hg19 UCSC human reference genome33 and to UCSC known genes using a spliced alignment tool. Genes were considered expressed if at least one read mapped uniquely to an annotated transcript. Geneset enrichment analysis was performed on detected genes and overrepresented Gene Ontologies were reported. Detailed bioinformatics methodology is available in the Methodology section of the Supporting Information.

Figure 9A:
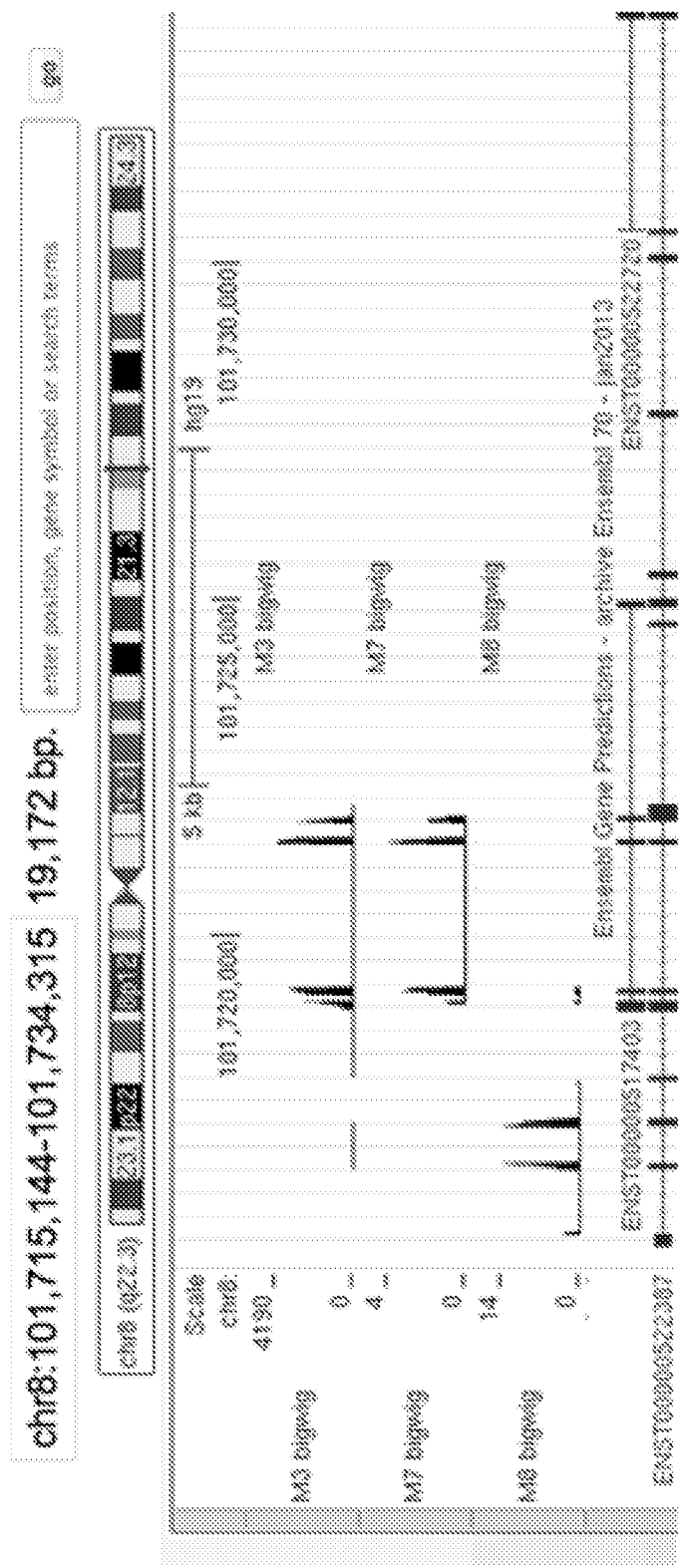
FIG. 9A-9B is a set of images displayed in the UCSC genome browser showing read coverage of RNA sequencing of aspirations. Genomic position is displayed along the X axis and depth of coverage is represented in the Y axis.
Figure 9B:
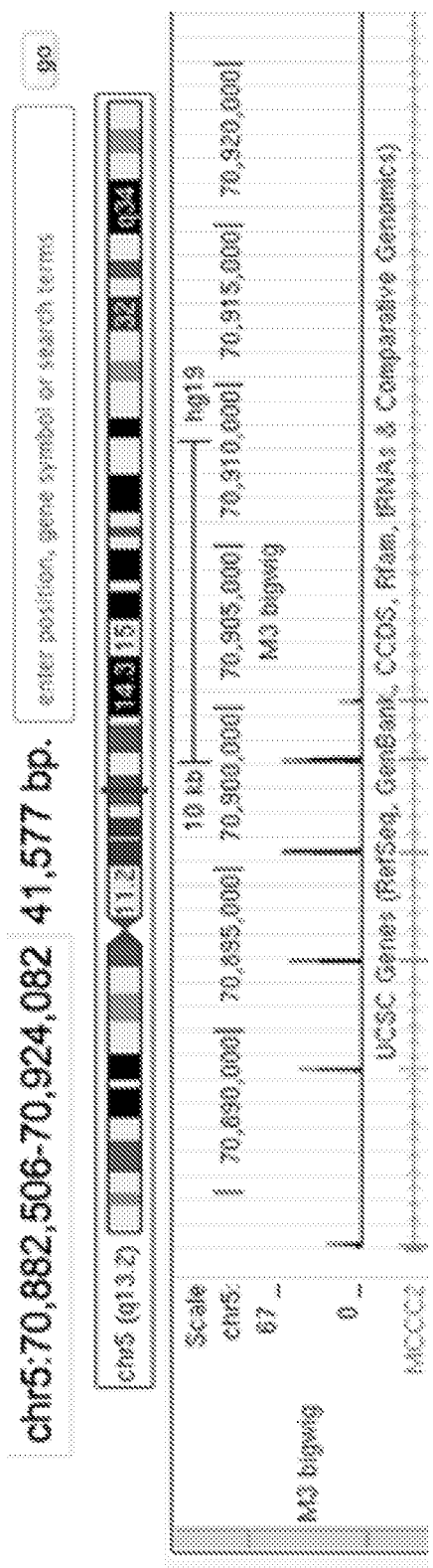

The nanobiopsy platform can be used to analyze endogenous mRNA expression from single living cells. cDNA of mature mRNA was generated, sequenced and the reads mapped to the human reference genome. Differential 3' untranslated region (UTR) usage in cytoplasmic Poly-A binding protein (PABPC1) was observed, where two aspirations show dominant expression of a noncanonical isoform, whereas the third shows expression of the canonical isoform (FIG. 9A). We have also observed instances where coverage was obtained over an entire transcript rather than just the 3' UTR. An example of read coverage over the full length of methylcrotonoyl-CoA carboxylase 2 (MCCC2) is shown in FIG. 9B. As another demonstration that nanobiopsy can be used to analyze endogenous RNAs, we enriched for the most overrepresented Gene Ontologies and found that two aspirations predominantly expressed machinery related to translation, while one was enriched for processes related to metabolism and morphogenesis.

Example 6

Sequencing of Genomes of Nanobiopsied Mitochondria

Figure 10:
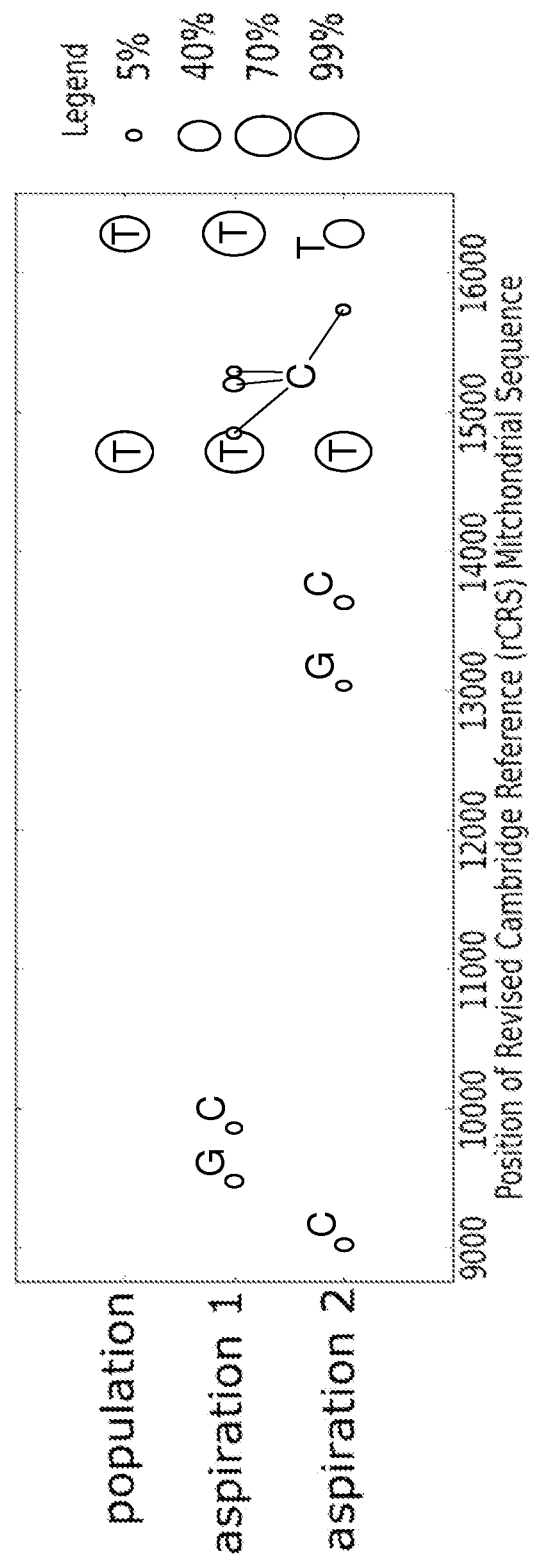
FIG. 10 is a plot depicting sequencing results from two mitochondria aspirations from a single cell, as well as DNA extracted from a population of cells. The sequencing results demonstrate variable conservation of heteroplasmic frequencies in aspirations. Heteroplasmic variants with estimated frequencies between 5% and 99% are displayed as circles where the area of the circle is proportional to the observed frequency. The nucleotide of the variant is indicated by the letter 'A,' 'C,' 'T,' or 'G' near or within the circle. The 14713 A->T variant shows similar frequencies across aspirations and population; whereas the 16278 C->T variant shows a greater variance of heteroplasmic frequencies in aspirations. Low frequency variants were also found in both aspirations, but not in the population.

Following biopsy of mitochondria as in Example 5, next-generation sequencing was employed to sequence the genomes of the biopsied mitochondria. The mitochondrial DNA was amplified using primers specific to the mitochondrial genome. This approach is novel and important because it allows us to selectively sequence the mitochondrial genome without the need to separate the mitochondrial nucleic acids from the more abundant nuclear DNA. Sequencing results from two mitochondria aspirations from a single cell, as well as DNA extracted from a population of cells revealed that the frequencies of some heteroplasmic variants are more conserved at the subcellular level (FIG. 10). For example, two heteroplasmic variants (14713 A->T and 16278 C->T) were found both in subcellular aspirations and samples from the total (pooled) mitochondrial population. Frequencies of the 14713 A->T variant were found to be similar across all samples, 83%, 87%, and 79%. However, the 16278 C->T variant showed substantial variation in frequencies with 62%, 98% and 38% frequencies for the pooled versus the selected mitochondria, respectively. Whereas the average heteroplasmic frequency is observable in population-based sequencing, only subcellular sequencing revealed heterogeneity of the variant within a cell. In addition to the differences in heteroplasmic frequencies among subcellular aspirations, we were also able to detect a number of variants that were >5% of sequencing reads. These results show that by a combination of the nanopipette with a novel mitochondrial directed genomic technology, small subpopulations of mitochondria genomes in single cells can be sequenced.

In Examples 5 and 6, nanobiopsy relies on the voltage-controlled aspiration of cellular material and not on adsorption to the nanopipette side walls. No amplification is observed if a negative voltage is not applied to the nanopipette after insertion into the cell and when aspiration is performed in the bulk solution. This is one key element that differentiates the nanobiopsy technology from AFM based platforms.

Example 7

A Nanopipette-PLA Based Instrument to Measure EGFR Signaling in MDA-MB-231 Cells.

EGFR activation leads to phosphorylation and stimulation of the MAPK and JNK pathways, multiple transcription factors (TFs) and ultimately changes in gene transcription and cell proliferation. Under basal conditions, many of the enzymes in these protein kinase pathways are inactive. However, EGF stimulation activates these proteins by switching their phosphorylation state. A multiplexed proximity ligand assay (PLA) is used to measure the phosphorylation of different components of the MAPK and JMNK EGFR signaling pathway. This includes the phosphorylation of MKK1, which catalyzes phosphorylation of the MAPKs ERK1/2 which then phosphorylate the TFs AP- and Fos-Jun, which regulate the expression of genes involved in cell growth.

For this specific example, PLAs for phosphorylated forms of JAK which stimulate phosphorylation of STATs which regulate cell proliferation are used. Various other phosphorylated target mediating EGF signaling may be studies, and one may conveniently acquire commercially available primary and secondary antibodies and generate antibody-oligonucleotide hybrids for use in PLA. PLAs are similarly developed to detect each purified phosphorylation target and optimized with regards to the amount of protein detected in solution.

One may use the nanopipette to sample varying amounts of cytoplasm from cells (e.g. individual MDA-MB-231 cells treated with EGF or clinical tumor cells) and assess the lowest amoun of cell sample needed for each PLA. One may also use the multiplex PLAs to measure changes in EGF signaling pathways in the cancer cells before and after EGF treatment in the same cell. The nanopipette setup is used to isolate separate samples from the same cell for PLA and WTA under basal conditions and after EGF stimulation. WTA can be used to identify gene clusters activated by EGF and changes in specific gene expression will be quantified by qPCR. The method may also be used to test selective inhibitors of MAPK or JNK that specifically block individual phosphorylation events and gene expression changes to provide a unique method to link specific signaling pathways in cancer cells to regulation of expression of selective genes.

Figure 11:
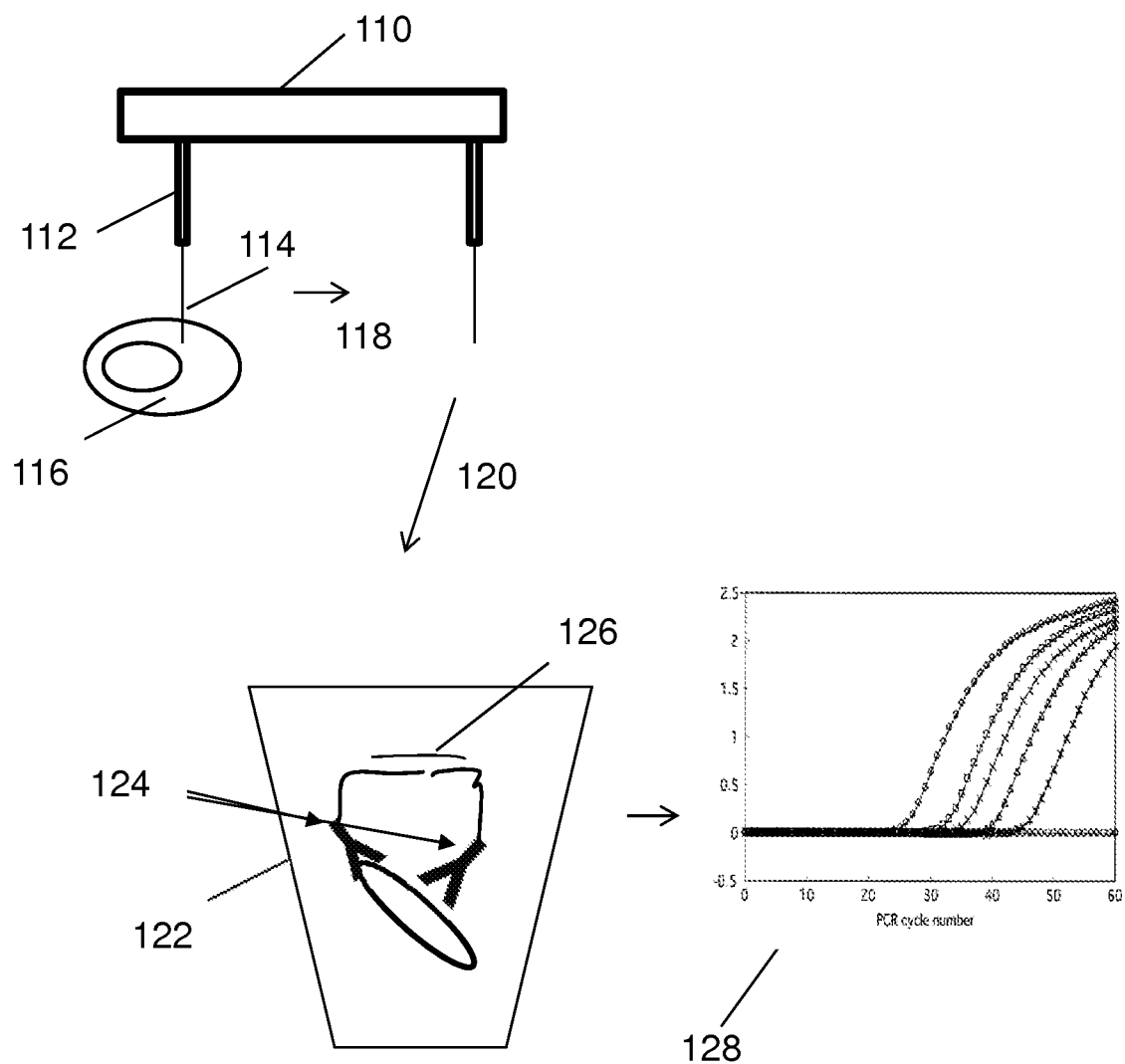
FIG. 11 is a schematic representation of a protein analysis of a single cell using the present nanopipette methods, wherein a specific protein is quantitated.

Referring now to FIG. 11, a mechanical platform 110 is used to support, direct, and manipulate a nanopipette 112, mounted on the platform 110, which further contains a microscopic guidance system and xyz controller for inserting the nanopipette tip 114 into a cell, 116. As shown, the cell 116 is eukaryotic, but the tip 114 is inserted into the cytosol compartment. Next, as shown at arrow 118, the nanopipette and contents aspirated from cell 116, are translocated to a container 122, as shown at arrow 120. Here, the protein or proteins of interest are allowed to bind to antibodies 124, which bind to separate epitopes on the same protein. For example, one epitope may be represented by a phosphorylated amino acids, are an other amino acid in the protein. As shown at 124, if the protein binds both antibodies, oligo tags will contact each other and allow ligation to each other. Then a primer 126 can be used to bridge the oligos and be amplified with the ligated oligos. The amplification, as shown at 128, can be carried out by a real-time or quantitative PCR process that detects the number of protein molecules that were amplified.

As shown in FIG. 11, a cell X is penetrated by a nanopipette mounted and guided by a microscope, e.g. an SICM (scanning ion conductive microscope). As described above, ~15 picoliter of cell content (~1%) is aspirated each time we use the nanopipette which corresponds to ~1 pg of total RNA. The sample is subjected to RNA amplification (~1000-fold) and used for cDNA synthesis and sequencing. The sample is also, or alternatively, the nanopipette instrumentation for single cell molecular analysis is to be able to conduct proteomic analysis in addition to genomic analysis in the same individual cells. PLA is an amplification assay employing antibodies to selectively detect individual protein targets It incorporates PCR to quantify the proteins. This is accomplished by fusing oligonucleotides used for PCR to the protein antibodies.

Again referring to FIG. 11, a schematic of the PLA portion of the present method is shown. schematic of the PLA. Two antibodies targeting different epitopes of the same protein are coupled to either a primer or a blocked oligonucleotide. Binding of the antibodies to the protein places each oligonucleotide in close proximity allowing for ligation and amplification. The amplified products can then be detected by real-time PCR. PLA has been used to measure a number of growth factor receptors including PDGFR and EGFR.

The PLA procedure is further For the EGFR it was used to study receptor dimerization, a critical first step in EGFR activation. Extensive studies have shown that PLA is over 1000-fold more sensitive than commercially available ELISAs and due to the PCR is able to detect relatively few target proteins in a sample. In situ PLA was sensitive enough to detect phosphorylated PDGFR β in fixed single cells and can measure drug induced inhibition of kinase activity.

In one approach, two different antibodies, one that selects for the phosphorylated target and the other that has a more general epitope on the same protein is used. For each set of antibodies, a primer oligonucleotide is coupled to one antibody and a blocking oligonucleotide will be coupled to the other. Hybridization of the two oligonucleotides will be accomplished using connector oligonucleotides. qPCR will be used to detect the amplified oligonucleotides in each PLA.

A second approach is based on a recently described technique (Weibrecht I, Grundberg I, Nilsson M, Soderberg O (2011) Simultaneous Visualization of Both Signaling Cascade Activity and End-Point Gene Expression in Single Cells. PLoS ONE 6(5): e20148. doi:10.1371/journal.pone.0020148) in which the oligonucleotides employed in the PLA are coupled to secondary antibodies. Thus, two antibodies targeting different epitopes of the same protein are used, as in the first approach, but they are from different species. Secondary antibodies from complementary species are coupled to either the primer or blocking oligonucleotide. The potential advantage of this approach is that rather than having to synthesize oligonucleotides to each antibody used in a multiplexed assay, only the secondary antibodies needed to be coupled to oligonucleotides and those secondary antibodies can be used commonly for each PLA. Initial studies in Aim 1 will determine which approach is most optimal for the assay development.

In another embodiment, multiplex the assays may be used, one determines the sensitivity of each assay to measure phosphoproteins in a common sample of cell homogenate (aspirate). The nanopipette is used to aspirate increasing amounts of cytoplasm for a single cell being studied and to determine the minimum amount of cell sample for which all of the PLAs can quantify their target proteins. One can vary the amount of sampling from individual cells by changing the voltage applied to the nanopipette tip. Optimally, it will be able to quantify each phosphoprotein in ~15 picoliter of cell content (~1% of the total cell), because this is the amount of cell sample we can measure WTA in these cancer cells and multiple sampling of this amount of cytosol can be aspirated without producing obvious harm to the cell or impair viability.

Using the above methods, one also determines status of a cell before and after being stimulated with a cell pathway activator. For example, sampling individual MDA-MB-231 cells before and 1 hr after EGF (1 uM) treatment and determining whether the PLAs will identify the expected increase in phosphorylation of the EGFR, MAPK and JAK pathways and AP-1/Jun and STAT TFs. Importantly, EGF can stimulate divergent signaling via MAPK-AP-1/Jun and JAK-STAT. Selective inhibitors of each of these pathways exist so that blocking one pathway should not affect EGF signaling via the other pathway to establish specificity of the phosphorylation.

To develop PLAs to measure phosphorylated EGFR, MKK1, ERK1/2, JAK, AP1/Jun and STAT, one can use commercially available antibodies from Cell Signaling (CS) Cell Signaling Technology, Inc. (CST) Beverly, Mass. and Santa Cruz Biotechnology, Inc., Dallas, Tex. (SC). For each target, two antibodies are to be used, one selectively targeting the phosphorylation site and the other antibody targeting a different epitope on the same protein. For the anti-EGFR antibody, one may use rabbit polyclonal 06-847 (CS) targeting amino acids 1156-1186 and mouse monoclonal 05-483 (CS) targeting tyrosine 1197. For MKK1, one may use the monclonal 04-376 (CS) that targets the C-terminal and the anti-phospho polyclonal 444995 that targets $pSer^{218/222}$ For ERK1/2, one may use the mouse monoclonal 05-1152 (CS) targeting residues 325-345 and an anti-phospho rabbit polyclonal targeting $pThr^{202}/Tyr^{204}$. For JAK1, one may use mouse monoclonal antibody A-9 (SC-1677) that targets residues 785-815 and rabbit anti-phospho antibody Tyr 1022 (SC-101716). To detect the phosphorylated TFs, one may use anti-c-Jun/AP-1 mouse monoclonal antibody OP55 (CS) and the rabbit anti-phospho monoclonal Y172 (CS) that targets phosphorylated $serine^{65}$ of c-Jun. For STAT1, one may use rabbit polyclonal SC-346 and mouse monoclonal anti-phospho-STAT1 (SC-8394) targeting $tyrosine^{701}$.

Synthesis of antibody-oligonucleotides may use previous procedures, cited above. Antibodies are reacted with a 30-fold excess of SMPB (Pierce). Excess SMPB is removed over a G-50 column. Primer oligonucleotide (5' thiol-AAA AAA AAA ATA TGA CAG AAC TAG ACA CTC TT) SEQ ID NO 5 and blocked oligonucleotide (5' thiol-AAA AAA AAA AGA CGC TAA TAG TTA AGA CGC TTU UU) SEQ ID NO: 6 are reacted with 10 mM DTT for 30 min, DTT is be removed and then the primer oligonucleotide with be added to one of the activated antibodies, the blocked oligonucleotide added to the other antibody of each set. Antibody-oligonucleotides are be purified by HPLC. For studies testing secondary antibody-oligonucleotide PLA probes, donkey anti-rabbit IgG (711-005-152, Jackson Immunoresearch) and donkey anti-mouse IgG (715-005-150, Jackson Immunoresearch) are used and conjugation of the oligonucleotides to the antibodies may be done in a similar fashion as described.

Purified targets (ex. phosphorylated EGFR) may be obtained from the same sources at the antibodies (SC or CS) and used to develop the PLAs. Protein targets, preincubated with the PLA probes for 1 hr and then reacted with a mixture containing probe ligation are connector oligonucleotides (5' phosphate-CTA TTA GCG TCC AGT GAA TGC GAG TCC GTC TAA GAG AGT AGT ACA GCA GCC GTC AAG AGT GTC TA SEQ ID NO: 7 (Eurogentec) and 5'-phosphate-GTT CTG TCA TAT TTA AGC GTC TTA A) SEQ ID NO: 8. For real-time PCR a mixture containing 80 μM ATP, 0.2 mM dNTPs, 0.5 μM primers, 200 nM probe for the 5' nuclease assay, and 1.5 units of platinum TaqDNA polymerase are added. The reactants are transferred to a real-time PCR instrument for temperature cycling: 95° C. for 2 min and then 95° C. for 15 sec and 60° C. for 60 sec, repeated 45 times.

For PLA using the secondary antibody PLA probes, protein targets are first be incubated with the primary antibodies (not coupled to oligonucleotides) described above. The unbound antibodies are e removed by washing and the secondary antibody PLA probes (both anti-rabbit and anti-mouse) are added to each primary antibody bound target. The PLA will then follow a similar procedure as described.

Each PLA can be optimized with regards to the amounts of PLA probes used, the reaction time, washing procedures and ligation and hybridization reactions. One may also vary the amount of target protein to identify the optimal protein concentration for qPCR. Similar studies employ homogenates of MDA-MB-231 cells or test cells stimulated with EGF as a source of phosphorylated EGF regulated targets to account for any cellular factors that may affect the PLAs. Specificity can be established by blocking each PLA with the antibody peptides.

One may use the nanopipette to sample varying amounts of cytoplasm from individual cells treated with EGF (e.g. MDA-MB-231) and assess the lowest amount of cell sample needed for each PLA to quantify phosphorylation of each target protein. Cell aspirates will vary from as low as ~15 picoliter, the amount used in our WTA, to the entire cellular content. For each PLA, one may develop a dose response of cell content versus quantification of protein by qPCR. The analysis should be repeated on 3-4 different cells to determine variability of the PLA readout.

Multiplexed PLAs to Quantify EGF Induced Protein Phosphorylation in Test (e.g. MDA-MB-231) Cells.

One may multiplex the PLAs developed above and test the protein markers of interest for the minimum amount of cell sample to measure phosphorylation (or other modification) of all of the protein targets in the cells. The nanopipette is used to aspirate increasing amounts of cell sample. Each sample is then be equally divided and added to the PLAs to measure each target protein. The goal is to determine the minimum amount of cell aspirate needed to provide an optimal readout of each of the target proteins in the cell. One then use that amount of cell aspirate in a standard assay to measure each of the components of the EGF signaling pathway. One then may use multiplex PLAs to measure changes in EGF signaling pathways in the cancer cells before and after EGF treatment. For this, the nanopipette will be used to inject carboxyfluroscene into individual cancer cells. The labeled cell will then be sampled 1 hr before EGF treatment and then 1 hr after EGF (1 µM) addition. The PLAs will detect major increases in the phosphorylation of the target proteins because under basal conditions, should there sufficient phosphorylation of each target protein. One may also aspirate multiple samples from untreated cancer cells to determine whether cell aspiration itself induces phosphorylation of the target proteins. If it does, one may use that stimulation as a baseline measure for determining effects of EGF stimulation.

To test the specificity of the PLAs to measure EGF signaling, we will determine whether inhibitors of the some of the kinases regulated by EGF block downstream kinase and TF phosphorylation in single MDA-MB-231 cells. First, one may determine whether the EGFR kinase inhibitor Gefitinib (1 µM) (Cayman Europe) blocks phosphorylation of EGFR, MKK1, ERK1/2, JAK, AP1/Jun and STAT. One may also test whether the MKK1 inhibitor PD0325901 (CS) selectively blocks MKK1, ERK1/2 and AP1/Jun phosphorylation without affecting EGFR, JAK and STAT phosphorylation. This compound blocks MKK1 activity and subsequent phosphorylation of ERK1/2 but does not directly interact with ERK1/2. As further aspects of the present method application to an uncharacterized tumor cell, one may test whether the ERK1/2 selective inhibitor FR180204 blocks ERK1/2 and AP1-Jun phosphorylation but not the other components of EGF signaling. Additional, one may test whether the JAKs inhibitor INCB018424 (Chemitek) blocks EGF induced phosphorylation of JAK and STAT but not EGF induced phosphorylation of the MAPK pathway.

It is expected that PLAs to detect EGFR, MKK1, ERK1/2, JAK, AP1/Jun and STAT phosphorylation will have about 1000-fold higher sensitivity than commercially available ELISAs to these proteins; in addition, a multiplex PLA format can detect these phosphoproteins in a single aspirate of 15-150 picoliters from a single cell; also, it is expected that EGF stimulation of a single tumor cell, particularly a triple negative cell, for example model cell MDA-MB-231, will induces a significant ($P<0.05$) increase in phosphorylation of the target proteins compared to non-treated controls.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

1. Schubert C (2011) Single-cell analysis: The deepest differences. *Nature* 480(7375):133-137.
2. Wang D & Bodovitz S (2010) Single cell analysis: the new frontier in 'omics'. *Trends in Biotechnology* 28(6): 281-290.
3. Zheng X T & Li C M (2012) Single cell analysis at the nanoscale. *Chemical Society Reviews* 41(6):2061-2071.
4. Trouillon R, Passarelli M K, Wang J, Kurczy M E, & Ewing A G (2012) Chemical Analysis of Single Cells. *Analytical Chemistry* 85(2):522-542.
5. Van Gelder R N, et al. (1990) Amplified RNA synthesized from limited quantities of heterogeneous cDNA. *Proceedings of the National Academy of Sciences* 87(5):1663-1667.
6. Eberwine J & Bartfai T (2011) Single cell transcriptomics of hypothalamic warm sensitive neurons that control core body temperature and fever response: Signaling asymmetry and an extension of chemical neuroanatomy. *Pharmacology & Therapeutics* 129(3):241-259.
7. Zong C, Lu S, Chapman A R, & Xie X S (2012) Genome-Wide Detection of Single-Nucleotide and Copy-Number Variations of a Single Human Cell. *Science* 338(6114):1622-1626.
8. Morris J, Singh J M, & Eberwine J H (2011) Transcriptome Analysis of Single Cells. *J Vis Exp* (50):e2634.
9. Yum K, Wang N, & Yu M-F (2010) Nanoneedle: A multifunctional tool for biological studies in living cells. *Nanoscale* 2(3):363-372.

10. Tian B, et al. (2010) Three-Dimensional, Flexible Nanoscale Field-Effect Transistors as Localized Bioprobes. *Science* 329(5993):830-834.
11. Singhal R, et al. (2011) Multifunctional carbon-nanotube cellular endoscopes. *Nat Nano* 6(1):57-64.
12. Yan R, et al. (2012) Nanowire-based single-cell endoscopy. *Nat Nano* 7(3):191-196.
13. Osada T, Uehara H, Kim H, & Ikai A (2003) mRNA analysis of single living cells. *Journal of Nanobiotechnology* 1(1):2.
14. Uehara H, Kunitomi Y, Ikai A, & Osada T (2007) mRNA detection of individual cells with the single cell nanoprobe method compared with in situ hybridization. *Journal of Nanobiotechnology* 5(1):7.
15. Nawarathna D, Chang R, Nelson E, & Wickramasinghe H K (2011) Targeted messenger RNA profiling of transfected breast cancer gene in a living cell. *Analytical Biochemistry* 408(2):342-344.
16. Nawarathna D, Turan T, & Wickramasinghe H K (2009) Selective probing of mRNA expression levels within a living cell. *Applied Physics Letters* 95(8):083117.
17. Novak P, et al. (2009) Nanoscale live-cell imaging using hopping probe ion conductance microscopy. *Nat Meth* 6(4):279-281.
18. Shevchuk A I, et al. (2012) An alternative mechanism of clathrin-coated pit closure revealed by ion conductance microscopy. *The Journal of Cell Biology* 197(4):499-508.
19. Hansma P, Drake B, Marti O, Gould S, & Prater C (1989) The scanning ion-conductance microscope. *Science* 243(4891):641-643.
20. Korchev Y E, Bashford C L, Milovanovic M, Vodyanoy I, & Lab M J (1997) Scanning ion conductance microscopy of living cells. *Biophysical journal* 73(2):653-658.
21. Vilozny B, Actis P, Seger R A, Vallmajo-Martin Q, & Pourmand N (2011) Reversible Cation Response with a Protein-Modified Nanopipette. *Analytical Chemistry* 83(16):6121-6126.
22. Actis P, et al. (2011) Voltage-Controlled Metal Binding on Polyelectrolyte-Functionalized Nanopores. *Langmuir* 27(10):6528-6533.
23. Actis P, et al. (2011) Reversible thrombin detection by aptamer functionalized STING sensors. *Biosensors and Bioelectronics* 26(11):4503-4507.
24. Actis P, Mak A, & Pourmand N (2010) Functionalized nanopipettes: toward label-free, single cell biosensors. *Bioanalytical Reviews* 1(2):177-185.
25. Actis P, Jejelowo O, & Pourmand N (2010) Ultrasensitive mycotoxin detection by STING sensors. *Biosensors and Bioelectronics* 26(2):333-337.
26. Adam Seger R, et al. (2012) Voltage controlled nanoinjection system for single-cell surgery. *Nanoscale* 4(19):5843-5846.
27. Laforge F O, Carpino J, Rotenberg S A, & Mirkin M V (2007) Electrochemical attosyringe. *Proceedings of the National Academy of Sciences* 104(29):11895-11900.
28. Dale S E C & Unwin P R (2008) Polarised liquid/liquid micro-interfaces move during charge transfer. *Electrochemistry Communications* 10(5):723-726.
29. Chen C-C, Zhou Y, & Baker L A (2012) Scanning Ion Conductance Microscopy. *Annual Review of Analytical Chemistry* 5(1):207-228.
30. Berridge M J, Bootman M D, & Roderick H L (2003) Calcium signalling: dynamics, homeostasis and remodelling. *Nat Rev Mol Cell Biol* 4(7):517-529.
31. Brini M & Carafoli E (2009) Calcium Pumps in Health and Disease. *Physiological Reviews* 89(4):1341-1378.
32. Soon W W, Hariharan M, & Snyder M P (2013) High-throughput sequencing for biology and medicine. *Mol Syst Biol* 9.
33. Ståhlberg A, Thomsen C, Ruff D, & Åman P (2012) Quantitative PCR Analysis of DNA, RNAs, and Proteins in the Same Single Cell. *Clinical Chemistry* 58(12):1682-1691.

What is claimed is:

1. A system for extracting target intracellular content from a single cell, comprising:
   (a) a nanopipette mounted on an xyz controller;
   (b) a first electrode positioned within the interior of the nanopipette;
   (c) a second electrode positioned outside of the nanopipette;
   (d) a current detecting circuit and a voltage control circuit, the current detecting circuit detecting ionic current between the first electrode and the second electrode and the voltage control circuit controlling flow of liquid into and out of the nanopipette; and (e) a computer comprising programming that:
    instructs the xyz controller to move the nanopipette in response to changes in ionic current sensed by the current detecting circuit; and
    position the nanopipette tip at a fixed distance from surface of the single cell and move the nanopipette at a speed of 100 μm/sec to penetrate the cell membrane of the single cell; and
    instructs the voltage control circuit to:
        (i) apply a first bias voltage that holds a first electrolyte solution in the nanopipette;
        (ii) apply a second bias voltage that causes influx of target intracellular content from within the single cell when the nanopipette is positioned at a location of the target intracellular content within the single cell; and
        (iii) apply a third bias voltage that causes efflux of the target intracellular content from the nanopipette.

2. The system of claim 1, wherein
said xyz controller is attached to the nanopipette for effecting mechanical movements of the nanopipette in submicron x and y steps, and effecting movement of said nanopipette in a z direction towards or away from the single cell, and,
said xyz controller further having electronic controls for controlling said mechanical movements according to user defined control and
said voltage control is configured to reverse voltage in said voltage control circuit when said xyz controller has positioned the nanopipette tip within the single cell.

3. The system of claim 1, where the first electrode comprises a silver material.

4. The system of claim 1, wherein the first electrode comprises the first electrolyte solution, wherein the first electrolyte solution comprises a hydrophobic liquid and an ionic material comprising a borate.

5. The system of claim 1, wherein the nanopipette is quartz.

6. A method for extracting a target intracellular content from an individual cell, comprising:
    (a) preparing a solution containing at least one cell having a target intracellular content for extraction;
    (b) providing the system of claim 1 and operating the system for:
        i. manipulating the nanopipette to approach said one cell by sensing a drop in ionic current through the tip of the nanopipette;
        ii. generating a positive voltage between the first electrode and the second electrode to prevent liquid from entering in the nanopipette during insertion into the cell;
        iii. positioning the nanopipette to penetrate a predetermined cellular location and inserting it into the cell at a speed of 100 μm/sec;
        iv. adjusting voltage between the first electrode and the second electrode in order to cause nanopipette influx and extract target intracellular content;
        v. further adjusting the voltage in order to prevent extracted target intracellular content from leaving the nanopipette; and
        vi. further adjusting the voltage to cause an efflux of the extracted target intracellular content to a sample container.

7. The method of claim 6 wherein the extracted target intracellular content comprises nucleic acids or proteins.

8. The method of claim 7 wherein the nucleic acids comprise DNA or RNA.

9. The method of claim 8 wherein the DNA is mitochondrial DNA.

10. The method of claim 6 wherein the voltages are one or more of (a) −100 to −1000 mV to cause influx of target intracellular content into the nanopipette;
    (b) 100-500 mV to stop influx and prevent efflux from the nanopipette; and
    (c) +0.5 to 2 V to cause efflux of the extracted target intracellular content.

11. The method of claim 10 wherein the influx in step (a) lasts between 1 and 5 seconds.

12. The method of claim 6 wherein the efflux is into a sample container containing a nucleic acid storage buffer.

13. The method of claim 6 wherein the extracted target intracellular content is DNA from a single mitochondrion and further comprising the step of determining a portion of the sequence of the mitochondrial DNA.

14. The method of claim 6, further comprising:
    analyzing the extracted target intracellular content by one or both of
    (i) analyzing mRNA from the extracted target intracellular content; and
    (ii) analyzing one or more selected proteins from the extracted target intracellular content.

15. The method of claim 14 wherein said analyzing mRNA includes analysis of at least 500 pg of mRNA from the cell.

16. The method of claim 14 wherein the analyzing mRNA includes analyzing at least 90% of the mRNA sequences in the cell.

17. The method of claim 14 wherein said analyzing a protein comprises an ultra-sensitive assay detecting a specific protein.

18. The method of claim 17 wherein the assay comprises proximity ligation.

19. The method of claim 14, wherein said analyzing a protein species comprises analyzing at least one of EGFR, MKK1, ERK1/2, JAK, AP1/Jun, and STAT.

20. The method of claim 14, further comprising distinguishing a phosphorylated protein from the same protein that is not phosphorylated.

21. The method of claim 14, wherein the analyzing is carried out multiple times on the same cell at different times.

22. The method of claim 21 further comprising distinguishing a phosphorylated protein from the same protein that is not phosphorylated.

23. The method of claim 14, wherein analyzing a protein species from the cell comprises distinguishing a protein having post-translational modification from the same protein that is not so modified.

24. The system of claim 3, wherein the silver material is silver tetrakis(4-chlorophenyl)borate (AgTBACl).

25. The system of claim 4, wherein the hydrophobic liquid is 1-2 dichlorethane.

26. The system of claim 4, wherein the ionic material comprising a borate is tetrahexylammonium tetrakis(4-chlorophenyl)borate (THATPBCl).

27. The method of claim 16 wherein said analyzing a protein species comprises analyzing at least one of EGFR, MKK1, ERK1/2, JAK, AP1/Jun, and STAT.

28. The method of claim 17 wherein said analyzing a protein species comprises analyzing at least one of EGFR, MKK1, ERK1/2, JAK, AP1/Jun, and STAT.

29. The method of claim 18 wherein said analyzing a protein species comprises analyzing at least one of EGFR, MKK1, ERK1/2, JAK, AP1/Jun, and STAT.

30. The method of claim 16, further comprising distinguishing a phosphorylated protein from the same protein that is not phosphorylated.

31. The method of claim 17, further comprising distinguishing a phosphorylated protein from the same protein that is not phosphorylated.

32. The method of claim 18, further comprising distinguishing a phosphorylated protein from the same protein that is not phosphorylated.

33. The method of claim 16, wherein the analyzing is carried out multiple times on the same cell at different times.

34. The method of claim 17, wherein the analyzing is carried out multiple times on the same cell at different times.

35. The method of claim 18, wherein the analyzing is carried out multiple times on the same cell at different times.

36. The method of claim 16, wherein analyzing a protein species from the cell comprises distinguishing a protein having post-translational modification from the same protein that is not so modified.

37. The method of claim 17, wherein analyzing a protein species from the cell comprises distinguishing a protein having post-translational modification from the same protein that is not so modified.

38. The method of claim 18, wherein analyzing a protein species from the cell comprises distinguishing a protein having post-translational modification from the same protein that is not so modified.

39. The system of claim 1, wherein the nanopipette comprises a hydrophobic electrolyte solution and the first electrode is in contact with the hydrophobic electrolyte solution.

40. The system of claim 39, further comprising a container comprising the cell in an aqueous solution and wherein the second electrode is positioned in the aqueous solution.

41. The system of claim 40, wherein the target intracellular content in the cell comprises an organelle, organelle content, or cytosolic content.

42. The system of claim 40, further comprising an optical microscope.

43. The system of claim 1, wherein the nanopipette tip has an inner diameter of 50 nm (±20%).

44. The system of claim 1, wherein the nanopipette tip has an inner diameter in the range of 40 nm-60 nm.

45. The system of claim 1, wherein the nanopipette tip has an inner diameter in the range of 10 nm-100 nm.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: Synthetically prepared oligonucleotide sequence

<400> SEQUENCE: 1
gcgccgaggt gaagttcgag g                                                 21

<210> SEQ ID NO 2
<211> LENGTH: 21
<212> TYPE: DNA
<213> ORGANISM: Artificial
<220> FEATURE:
<223> OTHER INFORMATION: Synthetically prepared oligonucleotide sequence

<400> SEQUENCE: 2
gccgtcgccg atgggggtgt t                                                 21

<210> SEQ ID NO 3
<211> LENGTH: 35
<212> TYPE: DNA
<213> ORGANISM: Artificial
<220> FEATURE:
```

```
<223> OTHER INFORMATION: Synthetically prepared oligonucleotide sequence

<400> SEQUENCE: 3
tcatttttat tgccacaact aacctcctcg gactc                              35

<210> SEQ ID NO 4
<211> LENGTH: 35
<212> TYPE: DNA
<213> ORGANISM: Artificial
<220> FEATURE:
<223> OTHER INFORMATION: Synthetically prepared oligonucleotide sequence

<400> SEQUENCE: 4
cgtgatgtct tatttaaggg gaacgtgtgg gctat                              35

<210> SEQ ID NO 5
<211> LENGTH: 32
<212> TYPE: DNA
<213> ORGANISM: Artificial
<220> FEATURE:
<223> OTHER INFORMATION: Synthetically prepared oligonucleotide sequence

<400> SEQUENCE: 5
aaaaaaaaaa tatgacagaa ctagacactc tt                                 32

<210> SEQ ID NO 6
<211> LENGTH: 35
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (33)..(35)
<223> OTHER INFORMATION: n = uridine

<400> SEQUENCE: 6
aaaaaaaaaa gacgctaata gttaagacgc ttnnn                              35

<210> SEQ ID NO 7
<211> LENGTH: 65
<212> TYPE: DNA
<213> ORGANISM: Artificial
<220> FEATURE:
<223> OTHER INFORMATION: Synthetically prepared oligonucleotide sequence

<400> SEQUENCE: 7
ctattagcgt ccagtgaatg cgagtccgtc taagagagta gtacagcagc cgtcaagagt   60
gtcta                                                               65

<210> SEQ ID NO 8
<211> LENGTH: 25
<212> TYPE: DNA
<213> ORGANISM: Artificial
<220> FEATURE:
<223> OTHER INFORMATION: Synthetically prepared oligonucleotide sequence

<400> SEQUENCE: 8
gttctgtcat atttaagcgt cttaa                                         25
```